US009353186B2

(12) United States Patent
Freiberg et al.

(10) Patent No.: US 9,353,186 B2
(45) Date of Patent: May 31, 2016

(54) NEUTRALIZING PROLACTIN RECEPTOR ANTIBODY MAT3 AND ITS THERAPEUTIC USE

(75) Inventors: Christoph Freiberg, Wuppertal (DE); Christiane Otto, Wuppertal (DE); Lars Linden, Düsseldorf (DE); Axel Harrenga, Wuppertal (DE); Mark Trautwein, Wülfrath (DE); Simone Greven, Dormagen (DE); Andreas Wilmen, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 91 days.

(21) Appl. No.: 14/123,517

(22) PCT Filed: May 31, 2012

(86) PCT No.: PCT/EP2012/060078
§ 371 (c)(1),
(2), (4) Date: Feb. 6, 2014

(87) PCT Pub. No.: WO2012/163932
PCT Pub. Date: Dec. 6, 2012

(65) Prior Publication Data
US 2014/0141003 A1    May 22, 2014

(30) Foreign Application Priority Data

Jun. 3, 2011   (EP) .................................... 11168644

(51) Int. Cl.
| | |
|---|---|
| *C07K 16/28* | (2006.01) |
| *A61K 39/395* | (2006.01) |
| *A61K 45/06* | (2006.01) |
| *A61K 39/00* | (2006.01) |

(52) U.S. Cl.
CPC ......... *C07K 16/2869* (2013.01); *A61K 39/3955* (2013.01); *A61K 45/06* (2013.01); *A61K 2039/505* (2013.01); *C07K 2317/21* (2013.01); *C07K 2317/33* (2013.01); *C07K 2317/34* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,510,245 A | 4/1985 | Cousens et al. | |
| 4,634,665 A | 1/1987 | Axel et al. | |
| 4,657,760 A | 4/1987 | Kung et al. | |
| 4,816,567 A | 3/1989 | Cabilly et al. | |
| 4,968,615 A | 11/1990 | Koszinowski et al. | |
| 5,168,062 A | 12/1992 | Stinski | |
| 5,179,017 A | 1/1993 | Axel et al. | |
| 5,206,344 A | 4/1993 | Katre et al. | |
| 5,225,212 A | 7/1993 | Martin et al. | |
| 5,766,886 A | 6/1998 | Studnicka et al. | |
| 6,300,064 B1 | 10/2001 | Knappik et al. | |
| 6,989,250 B2 | 1/2006 | Soderlind et al. | |
| 7,867,493 B2 | 1/2011 | Damiano et al. | |
| 2007/0269438 A1 | 11/2007 | Elenbaas et al. | |

FOREIGN PATENT DOCUMENTS

| | | |
|---|---|---|
| EP | 2332995 A1 | 6/2011 |
| WO | 03004989 A2 | 1/2003 |
| WO | 03008583 A3 | 1/2003 |
| WO | 2006110585 A2 | 10/2006 |
| WO | 2008022295 A2 | 2/2008 |

OTHER PUBLICATIONS

Gerlo et al., "Prolactin in man: a tale of two promoters," BioEssays, 2006, 28(10):1051-1055.
Wong et al., "A Phase I Radioimmunotherapy Trial Evaluating Yttrium-labeled Anti-Carcinoembryonic Antigen (CEA) Chimeric T84.66 in Patients with Metastatic CEA-producing Malignancies," Clinical Cancer Research, 2000, 6: 3855-3863.
Bole-Feysot et al., "Prolactin (PRL) and its receptor: actions, signal transduction pathways and phenotypes observed in PRL receptor knockout mice," Endocrine Reviews, 1998, 19(3):225-268.
Goffin et al., "Drug Insight: prolactin-receptor antagonists, a novel approach to treatment of unresolved systemic and local hyperprolactinemia?" Nature Clinical Practice Endocrinology and Metabolism, 2006, 2(10): 571-581.
Courtillot et al., "Characterization of two constitutively active prolactin receptor variants in a cohort of 95 women with multiple breast fibroadenomas," Journal of Clinical Endocrinology & Metabolism, 2010, 95(1):271-279.
Bogorad L. et al., "Identification of a gain-of-function mutation of the prolactin receptor in women with benign breast tumors," PNAS, 2008, 105(38),14533-14538.
Sissom et al., "Anti-growth action on mouse mammary and prostate glands of a monoclonal antibody to prolactin receptor," American Journal of Pathology, 1988, 133(3):589-595.
Martinez et al., "Prolactin receptor in human endometriotic tissues," Acta Obstetricia et Gynecologica Scandinavica, 2002, 81(1):5-10.
Roden et al., "Cardiac Ion Channels," Annu. Rev. Physiol, 2002, 64:47-67.
Sissom-DeMore et al., "A Monoclonal Antibody to Prolactin Receptor Inhibits Proliferation of Breast Cancer Cells," The FASEB Journal, 1996, 10(6), A1389.

(Continued)

*Primary Examiner* — Ruixang Li
(74) *Attorney, Agent, or Firm* — Thomas C. Blankinship; Yonggang Ji

(57) ABSTRACT

The neutralizing prolactin receptor antibody Mat3, and antigen binding fragments, pharmaceutical compositions containing them and their use in the treatment or prevention of benign disorders and indications mediated by the prolactin receptor such as endometriosis, adenomyosis, non-hormonal female contraception, benign breast disease and mastalgia, lactation inhibition, benign prostate hyperplasia, fibroids, hyper- and normoprolactinemic hair loss, and cotreatment in combined hormone therapy to inhibit mammary epithelial cell proliferation and for the treatment and prevention of antiestrogen-resistant breast cancer. The antibody blocks prolactin receptor-mediated signalling.

14 Claims, 14 Drawing Sheets

(56) References Cited

OTHER PUBLICATIONS

Alvarez-Nemegyei et al., "Bromocriptine in systemic lupus erythematosus: a double-blind, randomized, placebo-controlled study," Lupus, 1998, 7:414-419.
Wagner et al., "Administration Guidelines for Radioimmunotherapy of Non-Hodgkin's Lymphoma with Y-Labeled Anti-CD20 Monoclonal Antibody," J. Nuclear Med., 2002, 43:267-272.
Söderlind et al., "Recombining germline-derived CDR sequences for creating diverse single-framework antibody libraries," Nature BioTechnology, 2000, 18(8):852-856.
Ormandy et al., "Null mutation of the prolactin receptor gene produces multiple reproductive defects in the mouse," Genes and Development, 1997, 11:167-178.
Garzia et al., "Lack of expression of endometrial prolactin in early implantation failure: a pilot study," Human Reproduction, 2004, 19(8):1911-1916.
Perks et al., "Prolactin acts as a potent survival factor against C2-ceramide-induced apoptosis in human granulosa cells," Human Reproduction, 2003, 18(12):2672-2677.
Knappik et al., "Fully synthetic human combinatorial antibody libraries (HuCAL) based on modular consensus frameworks and CDRs randomized with trinucleotides," Journal of Molecular Biology, 2000, 296(1):57-86.
Kelly et al., "Implications of Multiple Phenotypes Observed in Prolactin Receptor Knockout Mice," Frontiers in Neuroendocrinology, 2001, 22:140-145.
Nevalainen et al., "Prolactin and Prolactin Receptors Are Expressed and Functioning in Human Prostate," J. Clin. Invest, 1997, 99(4):618-627.
Wennbo et al., "Transgenic Mice Overexpressing the Prolactin Gene Develop Dramatic Enlargement of the Prostate Gland," Endocrinology, 1997, 138(10):4410-4415.
Kindblom et al., "Prostate Hyperplasia in a Transgenic Mouse with Prostate-Specific Expression of Prolactin," Endocrinology, 2003, 144(6):2269-2278.
Naito et al., "Dihydrotestosterone inhibits murine hair growth via the androgen receptor," British Journal of Dermatology, 2008, 159:300-305.
Riva et al., "Loco-Regional Radioimmunotherapy of High-Grade Malignant Gliomas Using Specific Monoclonal Antibodies Labeled with Y: A Phase I Study," Clinical Cancer Research, 1999, 5:3275s-3280s.
Goffin et al., "Development of New Prolactin Analogs Acting as Pure Prolactin Receptor Antagonists," Pituitary, 2003, 6:89-95.
Niederfellner et al., "Epitope characterization and crystal structure of GA101 provide insights into the molecular basis for type I/II distinction of CD20 antibodies," Blood, 2011,118(2):358-368.
Roethlisberger, et al., "Domain Interactions in the Fab Fragment: A Comparative Evaluation of the Single-chain Fv and Fab Format Engineered with Variable Domains of Different Stability," Journal of Molecular Biology, 2005, 347:773-798.
Virnekas et al., "Trinucleotide phosphoramidites: ideal reagents for the synthesis of mixed oligonucleotides for random mutagenesis," Nucleic Acids Research,1994, 22(25): 5600-5607.
Khorana, et al., "Studies on Polynucleotides CIII Total Synthesis of the Structural Gene for an Alanine Transfer Ribonucleic Acid from Yeast, "J. Mol. Biol., 1972, 72:209-217.
Urlaub et al., "Isolation of Chinese hamster cell mutants deficient in dihydrofolate reductase activity," Proc. Natl. Acad., 1980, 77(7):4216-4220.
Kaufman et al., "Amplification and expression of sequences cotransfected with a modular dihydrofolate reductase complementary DNA gene," Mol. Biol., 1982, 159: 601-621.
Eskenazi et al., "Epidemiology of endometriosis," Obstet Gynecol Clin North Am., 1997, 24(2):235-58.
Gebel et al., "Spontaneous apoptosis of endometrial tissue is impaired in women with endometriosis," Fertility and Sterility, 1998, 69(6):1042-1047.
Ferrero et al., "Antiangiogenic therapies in endometriosis," British Journal of Pharmacology, 2006, 149:133-135.
Sinaii et al., "High rates of autoimmune and endocrine disorders, fibromyalgia, chronic fatigue syndrome and atopic diseases among women with endometriosis: a survey analysis," Human Reproduction, 2002, 17(10): 2715-2724.
Singtripop et al., "Suppression of the development of uterine adenomyosis by danazol treatment in mice," Life Sciences, 1992, 51(14):1119-1125.
Goehring et al., "Epidemiology of Benign Breast Disease, with Special Attention to Histologic Types," Epidemiologic Reviews, 1997, 19(2):310-327.
Courtillot et al., "Benign Breast Diseases," J Mammary Gland Biol Neoplasia, 2005, 10:325-335.
Banerjee et al., "Characterization of a monoclonal antibody against Human prolactin receptors," Int. J. Cancer, 1993, 55:712-721.
Tworoger et al., "Prolactin and breast cancer risk," Cancer Letters, 2006, 243:160-169.
Wennbo et al., "Activation of the Prolactin Receptor but Not the Growth Hormone Receptor is Important for Induction of Mammary Tumors in Transgenic Mice," J Clin Invest, 1997, 100:2744-2751.
Scatchard et al., "The Attractions of Proteins for Small Molecules and Ions," Ann N. Y. Acad. ScL, 1949, 51:660-672.
Sazinsky et al., "Aglycosylated immunoglobulin G1 variants productively engage activating Fc receptors," PNAS, 2008, 105(51):20167-20172.
Simmons et al., "Expression of full-length immunoglobulins in *Escherichia coli*: rapid and efficient production of aglycosylated antibodies," Journal of Immunological Methods, 2002, 263:133-147.
Hezareh et al., Effector Function Activities of a Panel of Mutants of a Broadly Neutralizing Antibody against Human Immunodeficiency Virus Type 1, Journal of Virology, 2001, 75(24):12161-12168.
Schuurman et al., "Normal human immunoglobulin G4 is bispecific: it has two different antigen-combining sites," Immunology, 1999, 97:693-698.
Allen et al., "Interchain Disulfide Bonding in Human IgG2 Antibodies Probed by Site-Directed Mutagenesis," Biochemistry, 2009, 48(17):3755-3766.
Köhler et al., "Continuous cultures of fused cells secreting antibody of predefined specificity," Nature, 1975, 256:495-497.
Johnson et al., "Kabat Database and its applications: 30 years after the first variability plot," Nucleic Acids Research, 2000, 28(1):214-218.
Chothia et al., "Canonical Structures for the Hypervariable Regions of Immunoglobulins," J. Mol. Biol., 1987, 196:901-917.
Zapata et al., "Engineering linear F(ab')2 fragments for efficient production in *Escherichia coli* and enhanced antiproliferative activity," Protein Engineering, 1995, 8(10):1057-1062.
Carlsson et al., "n-CoDeR concept: unique types of antibodies for diagnostic use and therapy," 2001, Expert Review of Molecular Diagnostics, 2001, 1(1):102-108.
Plückthun A., "The pharmacology of monoclonal antibodies: Antibodies from Escherichia coli," (Rosenberg, M., and Moore, G. P., eds) vol. 113:269-315.
Foitzik, Kerstin., "New Findings in the Treatment of Alopecia: The Influence of Prolactin, Retinoids and Transforming Growth Factor-β on Hair Growth," Aid Dermatol, 2005, 31(3):109-116.
Touraine et al., "Increased Expression of Prolactin Receptor Gene Assessed by Quantitative Polymerase Chain Reaction in Human Breast Tumors Versus Normal Breast Tissues," J Clin Endocrinol Metab, 1998, 83:667-74.
Harrison et al., "Diffuse hair loss: Its triggers and management," Cleveland Clinic Journal of Medicine, 2009, 76 (6):361-367.
Rossouw et al., "Risks and Benefits of Estrogen Plus Progestin in Healthy Postmenopausal Women: Principal Results From the Women's Health Initiative Randomized Controlled Trial," JAMA, 2002, 288(3):321-333.
Vorherr et al., "Fibrocystic breast disease: Pathophysiology, pathomorphology, clinical picture, and management," Am J Obstet Gynecol, 1986, 154:161-179.
Halme et al., "Retrograde Menstruation in Healthy Women and in Patients With Endometriosis," Obstet Gynecol, 1984, 64:151-154.
Retter et al., "VBASE2, an integrative V gene database," Nucleic Acids Research, 2005, 33:671-674.

Figure 1: Expression of prolactin in eutopic endometrium from patients and healthy controls and in endometriotic lesions
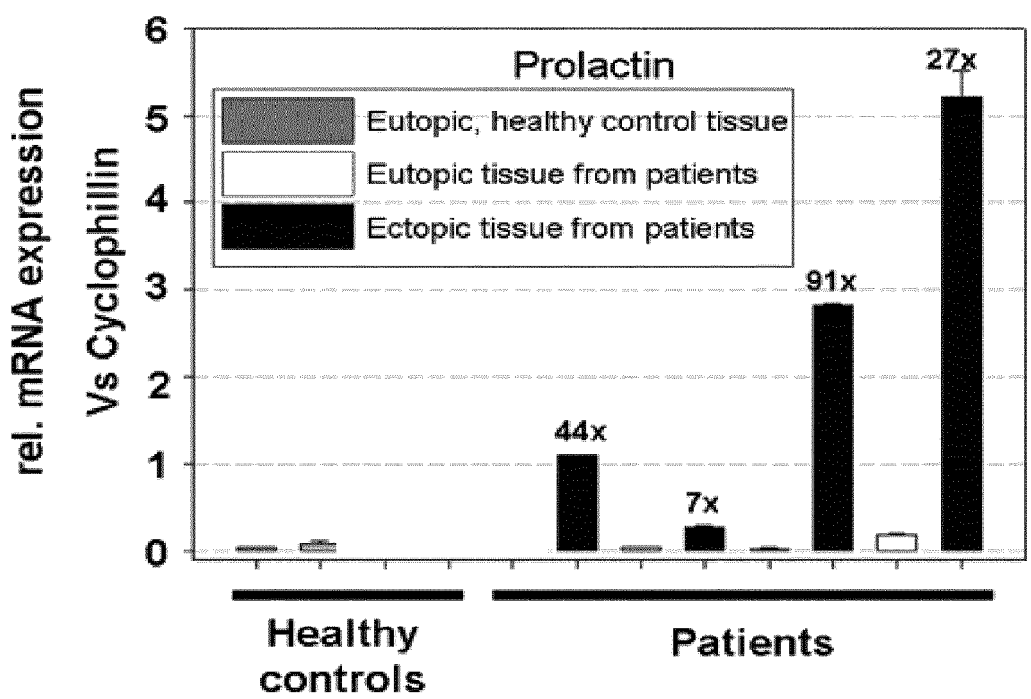

Figure 2: Expression of the prolactin receptor in eutopic endometrium from patients and healthy controls and in endometriotic lesions
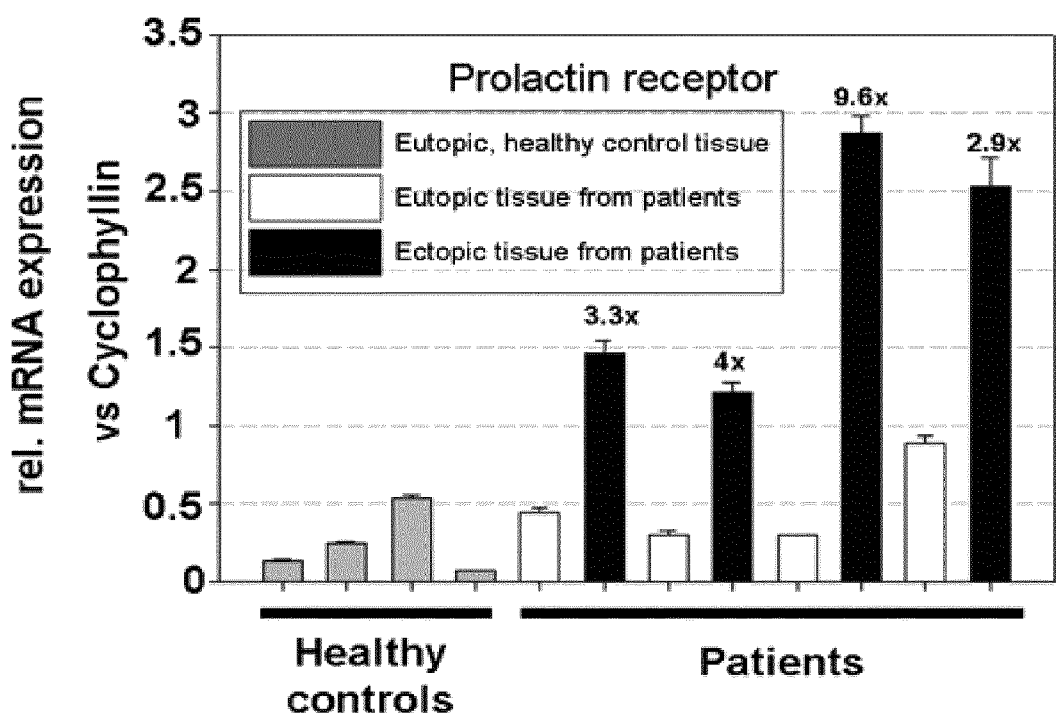

Figure 3: Effect of neutralizing PRLR antibody Mat3 in a hyperprolactinemic mouse model of benign breast disease
A    Inhibition of side-branching in the mammary gland by neutralizing PRLR antibody Mat3
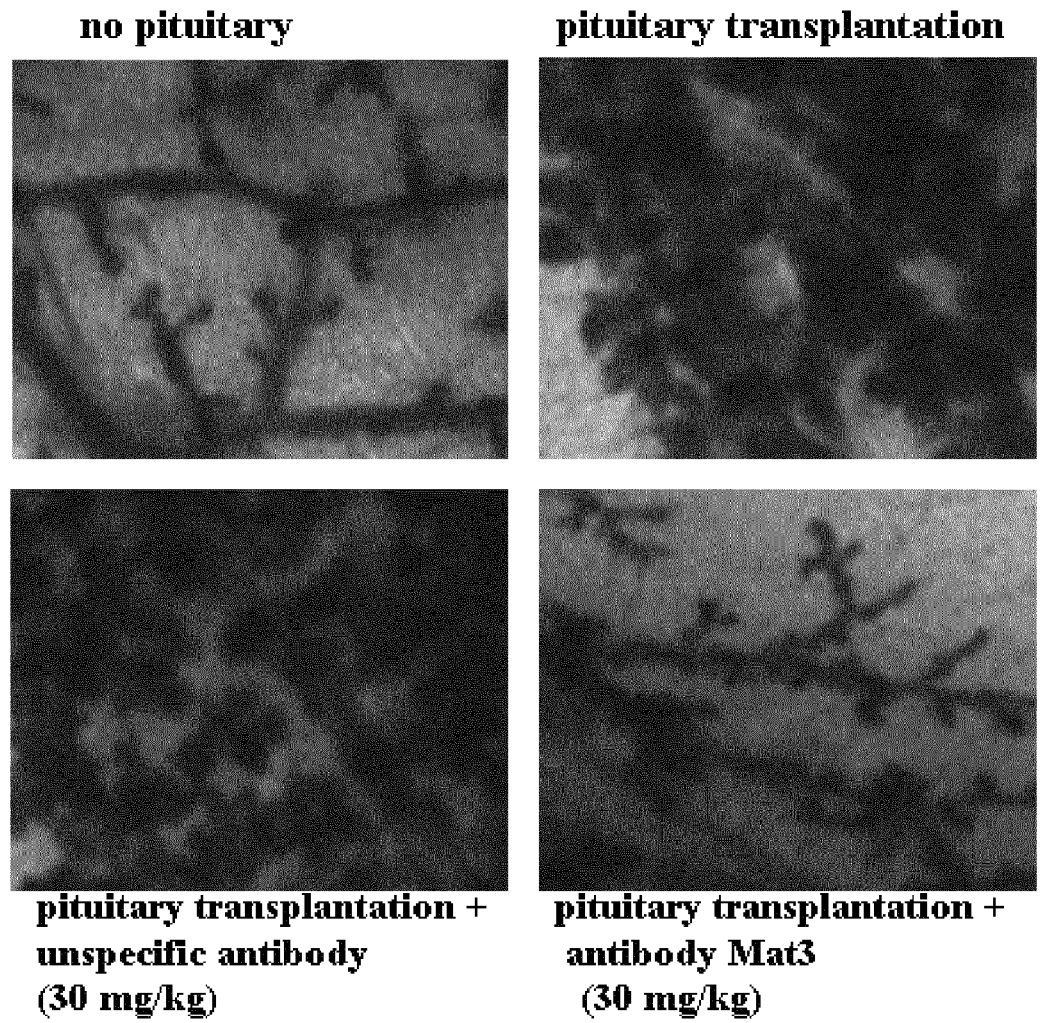

Figure 3: Effect of neutralising PRLR antibody Mat3 in a hyperprolactinemic mouse model of benign breast disease
B  Inhibition of the expression of the prolactin target gene elf5
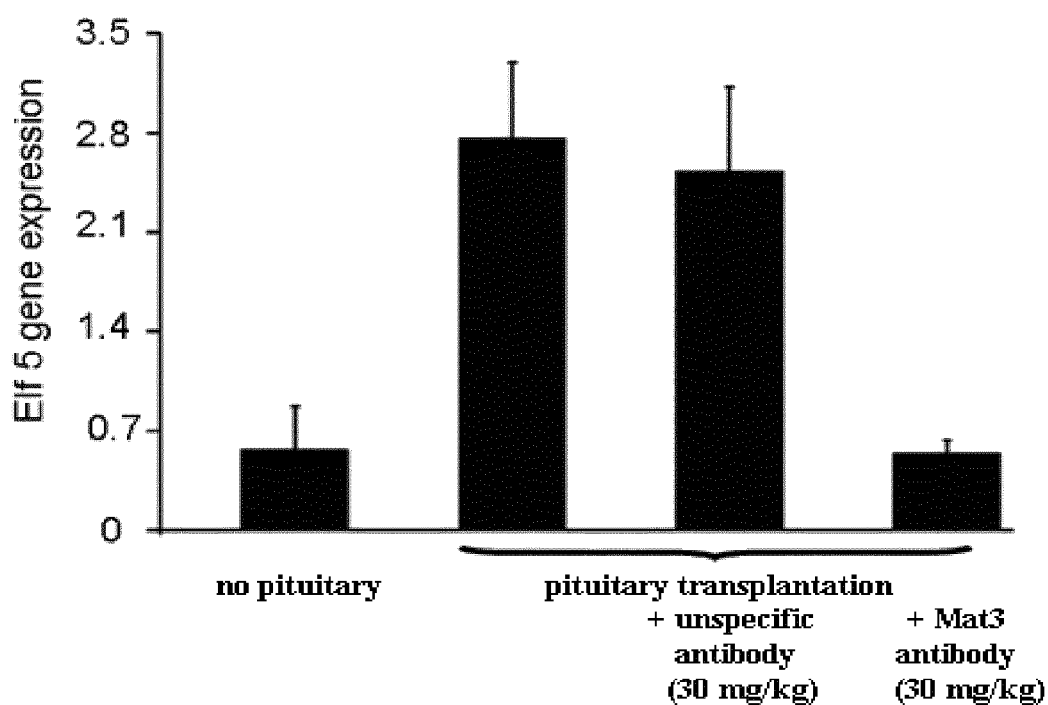

Figure 4: Kabat Numbering of framework amino acid positions according to Johnson and Wu (Nucleic Acids Res. 2000, 28, 214-218)

```
VL chain:

Kabat No.        L1  L2  L3  L4  L5  L6  L7  L8  L9  L11 L12 L13 L14 L15 L16 L17 L18 L19 L20 L21 L22 L23
LFR1             Q/D S/I V   L   T   Q   P   P   S   A   S   G   T   P   G   Q   R   V   T   I   S   C Kabat No.        L24 - L34
LCDR1            (X)n Kabat No.        L35 L36 L37 L38 L39 L40 L41 L42 L43 L44 L45 L46 L47 L48 L49
LFR2             W   Y   Q   Q   L   P   G   T   A   P   K   L   L   I   Y Kabat No.        L50 - L56
LCDR2            (X)n Kabat No.        L57 L58 L59 L60 L61 L62 L63 L64 L65 L66 L67 L68 L69 L70 L71 L72 L73 L74 L75 L76 L77 L78
LFR3             G   V   P   D   R   F   S   G   S   K   S   G   T   S   A   S   L   A   I   S   G   L Kabat No.        L79 L80 L81 L82 L83 L84 L85 L86 L87
LFR3             R   S   E   D   E   A   D   Y   Y Kabat No.        L88 - L97
LCDR3            (X)n Kabat No.        L98 L99 L100 L101 L102 L103 L104 L105 L106 L107 L108 L109
LFR4             F   G   G    G    T    K    L    T    V    L    G    Q VH chain:

Kabat No.        H1  H2  H3  H4  H5  H6  H7  H8  H9  H10 H11 H12 H13 H14 H15 H16 H17 H18 H19 H20 H21 H22
HFR1             E/Q V   Q/E L   E   S   G   G   G   L   V   Q   P   G   G   S   L   R   L   S   C Kabat No.        H23 H24 H25 H26 H27 H28
HFR1             A   A   S   G   F   T Kabat No.        H29 - H36
HCDR1            (X)n Kabat No.        H37 H38 H39 H40 H41 H42 H43 H44 H45 H46 H47
HFR2             V   R   Q   A   P   G   K   G   L   E   W Kabat No.        H48 - H66
HCDR2            (X)n Kabat No.        H67 H68 H69 H70 H71 H72 H73 H74 H75 H76 H77 H78 H79 H80 H81 H82 H82A H82B H82C H83 H84 H85
HFR3             F   T   I   S   R   D   N   S   K   N   T   L   Y   L   Q   M   N    S    L    R   A   E Kabat No.        H86 H87 H88 H89 H90 H91 H92
HFR3             D   T   A   V   Y   Y   C Kabat No.        H93 - H102
HCDR3            (X)n Kabat No.        H103 H104 H105 H106 H107 H108 H109 H110 H111 H112 H113
HFR4             W    G    Q    G    T    L    V    T    V    S    S
```

Figure 5A
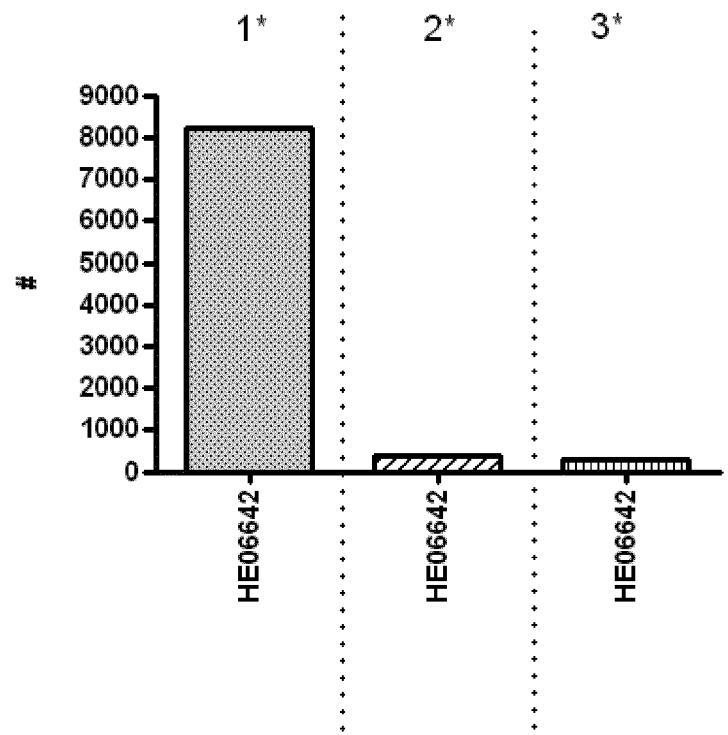
Figur 5B
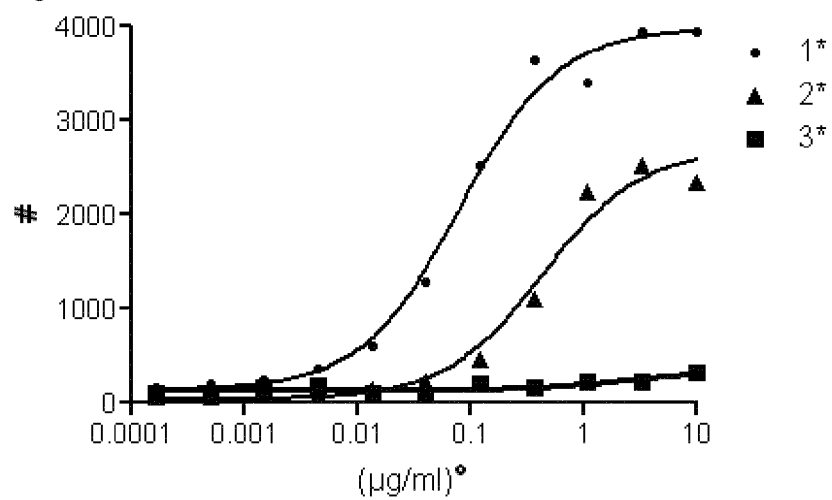

Figure 6A

```
                                                                    Section 1
                    (1)  1         10        20        30        46
        Mat3-VL     (1)  QSVLTQPPSASGTPGQRVTISCTGSSSNIGAGYVVHWYQQLPGTAP
VBASE2:humIGLV056   (1)  QSVLTQPPSVSGAPGQRVTISCTGSSSNIGAGYVVHWYQQLPGTAP
     Consensus     (1)  QSVLTQPPS SG PGQRVTISCTGSSSNIGAGYVVHWYQQLPGTAP
                                                                    Section 2
                   (47) 47        60        70        80        92
        Mat3-VL    (47) RLLIYRNNQRPSGVPDRFSGSKSGTSASLAISGLRSEDEADYYCAA
VBASE2:humIGLV056  (47) RLLIYGNSNRPSGVPDQFSGSKSGTSASLAITGLQSEDEADYYCKA
     Consensus    (47) RLLIY N  RPSGVPD FSGSKSGTSASLAI GL SEDEADYYC A
                                                                    Section 3
                   (93) 93   97
        Mat3-VL    (93) WDDSL
VBASE2:humIGLV056  (93) WDNSL
     Consensus    (93) WD SL
```

Figure 6B

```
                                                                    Section 1
                    (1)  1         10        20        30        46
        Mat3-VH     (1)  EVQLLESGGGLVQPGGSLRLSCAASGFTFSSYWMHWVRQAPGKGLE
VBASE2:humIGHV313   (1)  EVQLLESGGGLVQPGGSLRLSCAASGFTFSSYAMSWVRQAPGKGLE
     Consensus     (1)  EVQLLESGGGLVQPGGSLRLSCAASGFTFSSY M WVRQAPGKGLE
                                                                    Section 2
                   (47) 47        60        70        80        92
        Mat3-VH    (47) WVSDIARLSSYTNYADSVKGRFTISRDNSKNTLYLQMNSLRAEDTA
VBASE2:humIGHV313  (47) WVSVIYSGGSSTYYADSVKGRFTISRDNSKNTLYLQMNSLRAEDTA
     Consensus    (47) WVS I   S T YADSVKGRFTISRDNSKNTLYLQMNSLRAEDTA
                                                                    Section 3
                   (93) 93   98
        Mat3-VH    (93) VYYCAR
VBASE2:humIGHV313  (93) VYYCAK
     Consensus    (93) VYYCA
```

Figure 6C

```
                                                                    Section 1
                    (1)  1         10        20        30        45
      HE06442-VL    (1)  DIVLTQSPDSLAVSLGERATINCKASKSVSTSG--YTYMHWYQQK
VBASE2:humIGKV083   (1)  DIVMTQSPDSLAVSLGERATINCKSSQSVLYSSNNKNYLAWYQQK
     Consensus     (1)  DIV TQSPDSLAVSLGERATINCK S SV  S      Y  WYQQK
                                                                    Section 2
                   (46) 46        60        70        80        90
      HE06442-VL   (44) PGQPPKLLIYLASNRESGVPDRFSGSGSGTDFTLTISPVQAEDVA
VBASE2:humIGKV083  (46) PGQPPKLLIYWASTRESGVPDRFSGSGSGTDFTLTISSLQAEDVA
     Consensus    (46) PGQPPKLLIY AS RESGVPDRFSGSGSGTDFTLTIS  QAEDVA
                                                                    Section 3
                   (91) 91        100
      HE06442-VL   (89) TYYCQHSGEL
VBASE2:humIGKV083  (91) VYYCQQYYST
     Consensus    (91)   YYCQ
```

Figure 6D

```
                                                                                        Section 1
                    (1) 1          10         20         30              46
     HE06642-VH    (1) EVQLVESGGGLVQPGGSLRLSCAVSGFTFSSYGMSWVRQAPGKGLE
VBASE2:humIGHV313  (1) EVQLLESGGGLVQPGGSLRLSCAASGFTFSSYAMSWVRQAPGKGLE
      Consensus   (1) EVQL ESGGGLVQPGGSLRLSCA SGFTFSSY MSWVRQAPGKGLE
                                                                                        Section 2
                   (47) 47             60         70         80         92
     HE06642-VH   (47) WVATVSSGGTYTYYPDSVKGRFTISRDNSKNTLYLQMNSLRAEDTA
VBASE2:humIGHV313 (47) WVSVIYSGGSSTYYADSVKGRFTISRDNSKNTLYLQMNSLRAEDTA
      Consensus  (47) WV    SGG   TYY DSVKGRFTISRDNSKNTLYLQMNSLRAEDTA
                                                                                        Section 3
                   (93) 93     98
     HE06642-VH   (93) VYYCAR
VBASE2:humIGHV313 (93) VYYCAK
      Consensus  (93) VYYCA
```

NEUTRALIZING PROLACTIN RECEPTOR ANTIBODY MAT3 AND ITS THERAPEUTIC USE

SEQUENCE LISTING

The instant application contains a Sequence Listing which has been submitted in ASCII format via EFS-Web and is hereby incorporated by reference in its entirety. Said ASCII copy, created on Aug. 7, 2015, is named BHC113039-PCT-US_20150807_ST25.txt, and is 16,193 bytes in size.

The present invention is directed towards the prolactin receptor antibody Mat3 and provides recombinant antigen-binding regions of the antibody Mat3 and functional fragments containing such antigen-binding regions, that specifically bind and neutralize the prolactin receptor, nucleic acid sequences encoding the foregoing antibody, vectors containing the same, pharmaceutical compositions containing them and their use in the treatment or prevention of endometriosis and other diseases which benefit from inhibition of prolactin receptor mediated signalling.

Prolactin (PRL) is a polypeptide hormone composed of 199 amino acids. PRL belongs to the growth hormone (GH), placental lactogen (PL) family of polypeptide hormones and is synthesized in lactotroph cells of the pituitary and in several extrapituitary tissues such as lymphocytes, mammary epithelial cells, the myometrium, and the prostate. Two different promoters regulate pituitary and extrapituitary PRL synthesis (BioEssays 28:1051-1055, 2006).

PRL binds to the PRL receptor (PRLR), a single transmembrane receptor belonging to the class 1 cytokine receptor superfamily (Endocrine Reviews 19:225-268, 1998). The PRLR exists in three different isoforms, the short, the long, and the intermediate form that can be distinguished by the length of their cytoplasmic tails. Upon ligand binding, a sequential process leads to PRLR activation. PRL interacts via its binding site 1 with one PRLR molecule and then attracts via its binding site 2 a second receptor molecule leading to an active dimer of PRLRs. PRLR dimerization leads to the predominant activation of the JAK/STAT (Janus Kinase/Signal transducers and activators of transcription) pathway. Upon receptor dimerization, JAKs (predominantly JAK2) associated with the receptor, transphosphorylate and activate each other. In addition the PRLR is also phosphorylated and can bind to SH2-domain containing proteins such as STATs. Receptor bound STATs are subsequently phosphorylated, dissociate from the receptor and translocate to the nucleus where they stimulate transcription of target genes. In addition, activation of the Ras-Raf-MAPK pathway and activation of the cytoplasmic src kinase by PRLRs have been described (for review Endocrine Reviews 19: 225-268, 1998).

PRLR-mediated signalling plays a role in a variety of processes such as mammary gland development, lactation, reproduction, mammary and prostate tumor growth, autoimmune diseases, general growth and metabolism, and immunomodulation (Endocrine Reviews 19: 225-268, 1998; Annu. Rev. Physiol. 64: 47-67, 2002).

Currently, there is no medication available that enables complete interference with PRLR-mediated signalling beside the inhibition of pituitary PRL secretion by use of bromocriptine and other dopamine receptor 2 agonists (Nature Clinical Practice Endocrinology and Metabolism 2(10): 571-581, 2006). These agents, however, do not suppress extrapituitary PRL synthesis that can compensate successfully for the inhibition of pituitary PRL synthesis leading to almost unimpaired PRLR-mediated signalling (Endocrine Reviews 19:225-268, 1998). Therefore it is not surprising that dopamine type 2 receptor agonists were not beneficial in patients suffering from breast cancer or autoimmune diseases such as systemic lupus or rheumatoid arthritis (Breast Cancer Res. Treat. 14:289-29, 1989; Lupus 7:414-419, 1998) although prolactin has been implicated in these diseases. Local prolactin synthesis in breast cancer cells or lymphocytes which plays a pivotal role in mammary carcinoma or autoimmune diseases, respectively, was not blocked by dopamine receptor agonists.

Antibodies binding to PRLR for breast cancer diagnosis were described in WO2003/004989 (Millenium Pharmaceuticals) for the first time. In said WO03/004989 numerous genes and corresponding proteins including PRLR being overexpressed in several breast tumor tissues were regarded as suitable markers for early detection of malignancy. In WO03/008583, focussing on lymphoma and leukemia, carcinoma-associated genes and proteins are described including PRLR.

Furthermore, in WO2006/110585 (Novartis) PRLR overexpression as a cancer marker and the use of PRLR-specific antibodies for diagnosis and treatment of breast cancer and other cancer types (lung, prostate and skin cancer) were described. This time, monoclonal antibodies with antagonistic activity were claimed based on two experimental evidences: a) blocking of the PRLR expression by PRLR-specific siRNA in breast cancer MCF7 cells led to inhibition of proliferation of these cells and b) prolactin induces STAT5 and MAPK phosphorylation in breast cancer cells such as T47D. However, neither any evidence was provided that a monoclonal antibody indeed inhibited proliferation of breast cancer cell lines nor any concrete antibody was disclosed.

The first in vivo proof of concept that PRLR antagonists successfully interfere with breast cancer development has been published in 1988. In the DMBA mouse breast tumor model, a monoclonal PRLR antibody led to reduced incidence of mammary tumors (Am J Pathol 133:589-595, 1988).

First PRLR antibodies, claimed for the prevention and treatment of breast cancer, were described in US 2007/0269438 (Biogen). The expression products (antibodies) from five hybridoma cell lines were described by their ability to tightly bind breast cancer cell lines T47D and MCF7 and to block PRL-mediated signalling (STAT5-, MAPK-, AKT-phosphorylation). However, no in vivo proof of concept has been disclosed. Moreover, no evidence beyond the state-of-the-art knowledge has been provided for the statement that especially after the patient's cancer become antiestrogen-independent, the anti-PRLR antibody may be administered to the patient.

A second set of monoclonal PRLR-specific antibodies together with disclosed primary sequences was described in WO 2008/022295 (Novartis). Although these antibodies were claimed as therapeutic agents for breast, lung and prostate cancer, a lymphoma model served to show the antiproliferative effect of these agents in vivo.

On the other hand, peptidergic PRLR antagonists that are derived from prolactin and that carry an N-terminal deletion and a point mutation (e.g. delta1-9G129R prolactin) also behave as antagonists of the PRLR, however they suffer from reduced half-life time (15-20 min) and low potency if compared to prolactin (Pituitary 6:89-95, 2003). Therefore, neutralising PRLR antibodies are superior especially with regard to the inhibition of enhanced autocrine prolactin signalling that plays a role in breast cancer and prostate cancer.

The role of PRLR-mediated signalling was also investigated in the context of the benign disease endometriosis. In one study the expression pattern of the PRLR in endometriotic samples and eutopic endometrium from endometriosis patients was analysed (Acta Obstet Gynecol Scand 81:5-10, 2002) during the mid-late proliferative phase of the menstrual cycle. It was demonstrated that the PRLR mRNA was present in the eutopic endometrium in 79% of the analysed endometriosis patients, whereas it was absent in the endometriotic lesions in 86% of the endometriosis patients. These data suggested a possible differential regulation of PRLR expression between normal and endometriotic tissue. However, from these expression data it cannot be concluded that inhibition of the PRLR might represent a suitable endometriosis therapy—especially since the PRLR was not found to be expressed in the endometriotic lesions (Acta Obstet Gynecol Scand 81:5-10, 2002).

In conclusion, although PRLR-mediated signalling plays a role in a variety of cellular processes, very few and partially contradictory results have been disclosed demonstrating the therapeutic value of PRLR antagonism for most of the benign diseases including endometriosis.

Many data have been published indicating that PRLR might play a causative role in breast cancer. And conceptually, potent PRLR antagonists might be appropriate agents to demonstrate the therapeutic value of PRLR inhibition for breast cancer. Nevertheless, no in vivo proof of concept has been provided up to now that PRLR blockade indeed leads to inhibition of tumor growth (except lymphoma treatment and inhibition of breast cancer development) and moreover that antagonistic PRLR antibodies can be used for the treatment of benign diseases which benefit from blockade of PRLR signalling. Therefore, the antibodies currently available cannot be used in predictive models which allow pre-clinical proof-of-concept studies.

There is a need for antibodies which bind with high affinity to the PRLR in human, monkey and mouse without binding competitively to PRL and this way neutralize the PRLR-mediated signalling in all three species, and which allow to perform pre-clinical proof-of-concept studies in mouse as well as—at reasonable doses—also in monkey.

Therefore the underlying problem of the present invention lies in the provision of new PRLR antibodies which can be used in predictive models which allow pre-clinical proof of concept studies and which can be used for treatment of diseases which benefit from blockade of prolaction receptor signalling.

The problem is solved by the provision of the new antibody Mat3.

It has now been found that said antibody is surprisingly specific to and has a high affinity for PRLR in human, monkey and mouse in biochemical as well as cellular binding studies without binding competitively to PRL and this way neutralizes the PRLR-mediated signalling in all three species, in contrast to those antibodies as disclosed in WO 2008/022295, which bind non-competitively to PRL such as HE06642. This way, said antibody enables to perform pre-clinical proof-of-concept studies in mouse as well as—at reasonable doses—also in monkey. Moreover, it has now been found that said antibody can deliver a therapeutic benefit to the subject by being more potent and more closely related to human germline sequences and thus offers the opportunity of an improved side-effect profile, i.e. reduced risk of immunogenicity due to reduced dosage and increased similarity to human germline sequences, compared to those antibodies as disclosed in WO 2008/022295, which bind non-competitively to PRL such as HE06642.

The novel Mat3 antibody is preferably cross-reactive to PRLR from different species such as *Macaca mulatta* (rhesus monkey) and *Macaca fascicularis* (cynomolgus). *Mus musculus* (mouse) and *Homo sapiens* (human). Cross-reactivity here means that the affinities ($K_D$ values) and cell-binding $EC_{50}$ values of said antibody to human, monkey and mouse PRLR are below $10 \times 10^{-9}$M (see Table 1, examples 9, 10, 13 and 14) and proliferation inhibition $IC_{50}$ values are below $20 \times 10^{-9}$ M (see examples 1 to 3). The present invention is based on the discovery of the novel antibody Mat3 which can deliver a therapeutic benefit to the subject (sequences of the novel antibody are as in SEQ ID NO: 1-10). The antibody of the invention, which may be most preferably fully human with very close relationship to human germline sequences or which may be humanized or chimeric or human engineered variants thereof carrying the CDRs of the fully human version, can be used in many contexts which are more fully described herein.

To show superiority in potency and human-monkey-mouse cross-reactivity of said antibody over the most deeply characterized known antibody from WO 2008/022295 binding non-competitively to PRL, in in vitro proliferation studies the said antibody has been compared with HE06642 from WO 2008/022295 (Example 1-3). The here mentioned HE06642 or HE06.642 or 06.642 contains the variable domains SEQ ID NOs: 14 and 15, which are identical to the sequences of he06.642-2 in WO 2008/022295.

The antibody Mat3 was characterized in several cellular systems to determine its species specificity and its potency as well as efficacy in different readout paradigms addressing the inactivation of PRLR-mediated signalling and proliferation. Proliferation assays were performed in Ba/F cell lines either stably transfected with the human PRLR (Example 1), the murine PRLR (Example 2) or the rhesus PRLR (Example 3). Antibody Mat3 completely inhibited proliferation of cells carrying the human, the murine, and the rhesus PRLR (Example 1-3). Antibody HE06642 (WO 2008/022295) was inactive at the cells carrying the murine PRLR and showed strongly reduced activity at the rhesus PRLR-cells if compared with Mat3. Antibody Mat3 was also more potent at the human PRLR than antibody HE06.642. There is also evidence that Mat3 inhibits rat NB2 lymphomy cell proliferation with higher potency than HE06422. In addition to cellular proliferation assays, luciferase reporter assays were performed using HEK293 cell lines stably transfected with either the human or murine PRLR (Example 12) and transiently transfected with a luciferase reporter gene under the control of LHRE's (lactogenic hormone response elements). Using these systems, it could be confirmed that a promoter dependent on PRLR-mediated signalling is switched off in the presence of Mat3. The inability of the antibody HE06.642 to efficiently block murine PRLR-mediated signalling became evident again.

In conclusion, antibody Mat3 is therefore suitable for testing the inhibition of PRLR-mediated signalling in murine and monkey models.

The antibody contains variable domains being more similar to translated human germline V-genes than HE06642. FIG. 6 shows that the VH and VL domain are each 90% identical to the translated human germline heavy chain V and lambda light chain V genes [VBASE2 database; Retter I, Althaus H H, Münch R. Müller W: VBASE2, an integrative V gene database. Nucleic Acids Res. 2005 Jan. 1; 33 (Database issue):D671-4]. HE06642 exhibits 89% identity to the most similar translated VH germline sequence and only 80% identity to the most similar translated germline kappa light chain V sequence found in VBASE2. This finding offers the opportunity of having a lower immunogenicity risk when treating patients with Mat3.

Binding studies of Mat3 and HE06642 with the extracellular domains of human, monkey and mouse PRLR indicate that both antibodies interact with these purified domains (see below, Example 10 and Table 1). However, when these domains are exposed on cell surfaces more pronounced differences between Mat3 and HE06642 can be observed. Most strikingly, HE06642 does not bind murine PRLR when Ba/F cells express this receptor, while Mat3 does (Table 2, and FIG. 5, and Example 9). This finding is consistent with the observation that Mat3 blocks murine PRLR-mediated signalling and proliferation in contrast to HE06642. A peptide scan with the extracellular domain of the human PRLR, which is bound by Mat3 and HE06642 when purified as well as when exposed on cell surfaces, revealed that Mat3 binds to the subdomain 82 (Example 11) such as HE06642 as reported previously (WO 2008/022295). This scan additionally showed that there are differences in binding to the 82 domains between Mat3 and HE06642 (FIG. 8). Recently, it was published that different binding of antibodies observed by such a peptide scan enabled to explain differences of the antibodies' properties (Niederfellner et al., Blood. 2011, March 28. doi:10.1182/blood-2010-09-305847). In conclusion, the peptide scan results indicate why the antibody Mat3 shows a different species-specificity and potency compared to HE06642.

Provided is a human monoclonal antibody Mat3 according to table 5 (SEQ ID NO. 1-10) or antigen-binding fragments thereof which antagonize prolactin receptor-mediated signalling. The antibody specifically binds to the extracellular domain (ECD) of PRLR (SEQ ID NO: 12) or human polymorphic variants of SEQ ID No: 12 such as the 1146L and 176V variants being described in PNAS 105 (38), 14533, 2008, and J. Clin. Endocrinol. Metab. 95 (1), 271, 2010. Moreover, the antibody specifically binds to the extracellular domain (ECD) of rhesus and cynomulgus monkey PRLR (SEQ ID NO: 11) as well as murine PRLR (SEQ ID NO: 13).

In one embodiment human antibody Mat3, or humanized, human-engineered or chimeric antibody or antigen-binding fragment thereof are disclosed whereby the antibody comprises a variable heavy region corresponding with a nucleic acid sequence according to SEQ ID NO: 3, and an amino acid sequence according to SEQ ID NO: 1, and a variable light region with a nucleic acid sequence according to SEQ ID NO: 4, and an amino acid sequence according to SEQ ID NO: 2 which antagonize prolactin receptor-mediated signalling.

In one embodiment an antibody or antigen-binding fragment comprising the CDRs of the antibody as described above, whereby
the variable heavy chain contains the CDR sequences corresponding to SEQ ID NO: 5, 6, and 7 and the variable light chain contains the CDR sequences corresponding to SEQ ID NO: 8, 9, and 10.

In another embodiment of the present invention the antibody Mat3 consists of an antigen-binding region that binds specifically to one or more regions of the extracellular domain of PRLR from human, monkey and mouse, and whereby the amino acid sequences of the human PRLR are depicted by the amino acid sequences from position 1 to 210 of SEQ ID NO: 12 and human polymorphic variants of SEQ ID NO: 12, by the amino acid sequences from position 1 to 210 of the monkey PRLR according to SEQ ID NO: 11 and of the mouse PRLR according to SEQ ID NO: 13.

In another embodiment of the present invention the Mat3 consists of an antigen-binding region whereby the affinity to the extracellular domain of PRLR from human, monkey and mouse is at least 100 nM, preferably less than about 100 nM, more preferably less than about 30 nM, even more preferred less than about 10 nM.

In another embodiment the antibody Mat3 consists of an antigen-binding region that binds specifically to one or more regions of the extracellular domain of human PRLR and whereby the affinity is at least 10 nM, more preferable less than about 1 nM.

Also object of the present invention is the aforementioned Mat3, wherein the heavy chain constant domains determine a modified or unmodified IgG1, IgG2, IgG3 or IgG4.

Table 1 provides a summary of dissociation constants (affinities) and dissociation rates of the antibody Mat3 of the invention, as determined by surface plasmon resonance (Biacore) with monomeric extracellular domains (amino acid 1- to 210) of human PRLR (SEQ ID NO: 12), rhesus and cynomolgus PRLR (SEQ ID NO: 11, whereby the Fc-His fusion has been removed by proteolytic Factor Xa digestion) and murine PRLR (SEQ ID NO: 13) on the directly immobilized antibody (Example 10).

TABLE 1

Monovalent dissociation constants and dissociation rates of the extracellular domain of human, rhesus/cynomolgus monkey and mouse PRLR expressed in HEK293 cells determined for Mat3 as human IgG molecule by surface plasmon resonance (see Example 10)

|  | Human PRLR | Rhesus/Cynomolgus PRLR | Mouse PRLR |
|---|---|---|---|
| $K_D$ [M] | $0.9 \times 10^{-9}$ | $7.1 \times 10^9$ | $0.4 \times 10^9$ |
| $K_d$ [1/s] | $4.4 \times 10^{-4}$ | $1.1 \times 10^{-3}$ | $2.1 \times 10^{-4}$ |

The affinities disclosed for HE06642 in WO 2008/022295 are $2.6 \times 10^{-9}$ M on the extracellular domain of human PRLR, $38.9 \times 10^{-9}$ M on the corresponding domain of cynomolgus PRLR and $2.7 \times 10^{-9}$ M on the corresponding domain of murine PRLR.

The cell-based affinity of the antibody Mat3 was determined by fluorescence-activated cell sorting (FACS) combined with Scatchard analysis (Example 9).

Table 2 denotes the binding strength of Mat3 as human IgG2 molecule on the HEK293 cell line stably transfected with human and rhesus monkey PRLR, respectively.

TABLE 2

Cell-based binding potency of anti-PRLR antibody Mat3 in IgG2 format determined by FACS on the HEK293 cell line stably transfected with human and Rhesus monkey PRLR, respectively (see Example 9)

| | $EC_{50}$ [M] | |
|---|---|---|
| Antibody | HEK293 expressing human PRLR | Ba/F expressing rhesus monkey PRLR |
| Mat3 | $0.53 \times 10^{-9}$ | $2.94 \times 10^{-9}$ |

Antibody Generation

To isolate a panel of antibodies able to functionally block the human and murine PRLR, two formats of the synthetic human antibody phage display library called n-CoDeR® from Bioinvent (Söderlind et al. 2000, Nature BioTechnology. 18, 852-856), expressing scFv and Fab fragments, respectively, were investigated in parallel. The targets used for scFv or Fab selection were the soluble ECD of human PRLR (amino acid positions 1 to 210 of SEQ ID NO. 12) and mouse PRLR (amino acid positions 1 to 210 of SEQ ID NO: 13), applied as biotinylated (NHS-LC biotin, Pierce) and as non-biotinylated variant as well as the human breast cancer cell line T47D expressing PRLR.

A combination of various approaches in phage-display technology (PDT) was used to isolate high affinity, PRLR-specific, human monoclonal antibodies, by a combination of protein and whole cell pannings and through the development of specific tools. The panning tools and screening methods include the ECD of the human and mouse PRLR recombinantly expressed in fusion with an Fc domain (R&D Systems, catalogue no. 1167-PR and 1309-PR, respectively; pos. 1-216 of SEQ ID NO: 12 and 13, respectively, each fused to the human IgG1 Fc domain, pos. 100 to 330 of human IgG1), the extracellular domain of the human PRLR recombinantly expressed in fusion with a six-histidine tag (SEQ ID NO: 12), the HEK293 and the murine lymphoma cell line Ba/F each stably transfected with human and murine PRLR, respectively, and the breast cancer cell line T47D and the rat lymphoma cell Nb2 each naturally expressing PRLR as well as the development of panning procedures and screening assays capable of identifying neutralizing antibodies that preferentially bind to PRLR displayed on the cell surface and that are cross-reactive to PRLR from mouse.

Screening was performed by first identifying binders for human PRLR and eventually mouse PRLR in ELISA tests using recombinantly expressed antigens. The combination of these specific methods allowed the isolation of—amongst others—the antibody "005-C04".

By affinity maturation of "005-C04" on the extracellular domains of human PRLR and murine PRLR, beneficial substitutions were identified according to the procedure described in Example 8. Finally, individual substitutions beneficial for improved affinity were evaluated regarding their influence on thermostability of the antibody. Especially, cooperative unfolding of the Fab domain during denaturation of the matured antibodies (e.g. by temperature elevation) should have been ensured (reference regarding cooperative unfolding: Roethlisberger. D. et al., J. Mol. Biol. 2005: 347, 773-789). The antibody Mat3 resulted from the above described antibody discovery and maturation approach.

Peptide Variants

Antibodies of the invention are not limited to the specific peptide sequences provided herein. Rather, the invention also embodies variants of these polypeptides. With reference to the instant disclosure and conventionally available technologies and references, the skilled worker will be able to prepare, test and utilize functional variants of the antibodies disclosed herein, while appreciating that variants having the ability to bind und to functionally block PRLR fall within the scope of the present invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions (VH: HFR1, HFR2, HFR3, HFR4; VL: LFR1, LFR2, LFR3, LFR4) and three interspaced CDRs (VL: LCDR1, LCDR2, LCDR3; VH: HCDR1, HCDR2, HCDR3). The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

FIG. 4 provides the schemes for numbering each amino acid position in the variable domains VL and VH. Tables 3 (VH) and 4 (VL) delineate the CDR regions for antibody Mat3 of the invention and compare amino acids at a given position to a corresponding consensus or "master gene" sequence, in which the CDR regions are marked with 'X'. Table 5 and 6 help to assign the SEQ ID Numbers to the antibodies, antibody fragments and PRLR variants provided in this invention.

TABLE 3

VH Sequence of antibody Mat3 including CDR annotation

```
                                                |-HCDR1--|           |
Mat3 VH    EVQLLESGGG LVQPGGSLRL SCAASGFTFS S.YWMHWVRQ APGKGLEWVS
Consensus  EVQLLESGGG LVQPGGSLRL SCAASGFTXX XXXXXXXVRQ APGKGLEWVX ----HCDR2----------|                                   |-
Mat3 VH    DIARL.SSYT NYADSVKGRF TISRDNSKNT LYLQMNSLRA EDTAVYYCAR
Consensus  XXXXXXXXXX XXXXXXXXXF TISRDNSKNT LYLQMNSLRA EDTAVYYCXX --HCDR3-------|
Mat3 VH    GLDA.....R RMDYWGQGTL VTVSS
Consensus  XXXXXXXXXX XXXXWGQGTL VTVSS
```

TABLE 4

VL Sequence of antibody Mat3 including CDR annotation

```
                         |---LCDR1-----|
Mat3 VL    QSVLTQPPSA SGTPGQRVTI SCTGSSSNIG AGYVVHWYQQ LPGTAPKLLI
Consensus  QSVLTQPPSA SGTPGQRVTI SCXXXXXXXX XXXXXXWYQQ LPGTAPKLLI

|LCDR2|                                    |----LCDR3--
Mat3 VL    YRNNQRPSGV PDRFSGSKSG TSASLAISGL RSEDEADYYC AAWDDSLNG.
Consensus  YXXXXXXXGV PDRFSGSKSG TSASLAISGL RSEDEADYYX XXXXXXXXX -|
Mat3 VL    WLFGGGTKLT VLGQ
Consensus  XXFGGGTKLT VLGQ
```

TABLE 5

Sequences of the antibodies

| Antibody | HCDR1 SEQ ID | HCDR2 SEQ ID | HCDR3 SEQ ID | LCDR1 SEQ ID | LCDR2 SEQ ID | LCDR3 SEQ ID | VH Protein SEQ ID | VL Protein SEQ ID | VH Nucleotide SEQ ID | VL Nucleotide SEQ ID |
|---|---|---|---|---|---|---|---|---|---|---|
| Mat3 | 5 | 6 | 7 | 8 | 9 | 10 | 1 | 2 | 3 | 4 |
| HE06.642 | — | — | — | — | — | — | 14 | 15 | 16 | 17 |

TABLE 6

Sequences of the extracellular domains of PRLR from human, monkey and mouse

| Antibody | SEQ ID |
|---|---|
| Human ECD PRLR (Protein) | 12 |
| Murine ECD PRLR (Protein) | 13 |
| Rhesus and cynomolgus monkey ECD PRLR (Protein) | 11 |

The skilled worker can use the data in Tables 3, 4 and 5 to design peptide variants that are within the scope of the present invention. It is preferred that variants are constructed by changing amino acids within one or more CDR regions; a variant might also have one or more altered framework regions (FR). For example, a peptide FR domain might be altered where there is a deviation in a residue compared to a germline sequence.

Furthermore, variants may be obtained by maturation, i.e. by using one antibody as starting point for optimization by diversifying one or more amino acid residues in the antibody, preferably amino acid residues in one or more CDRs, and by screening the resulting collection of antibody variants for variants with improved properties. Particularly preferred is diversification of one or more amino acid residues in LCDR3 of VL. HCDR3 of VH, LCDR1 of VL and/or HCDR2 of VH. Diversification can be done by synthesizing a collection of DNA molecules using trinucleotide mutagenesis (TRIM) technology [Virnekäs, B., Ge, L. Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600; see also Example 8].

Conservative Amino Acid Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

As used herein, "sequence identity" between two polypeptide sequences, indicates the percentage of amino acids that are identical between the sequences. "Sequence homology" indicates the percentage of amino acids that either are identical or that represent conservative amino acid substitutions. Preferred polypeptide sequences of the invention contain amino acid sequences, whereby a. the amino acid sequence of the HCDR1 is identical to SEQ ID NO: 5 in at least 7 of 8 amino acids, and b. the amino acid sequence of the HCDR2 is identical to SEQ ID NO: 6 in at least 14 of 19, more preferred 15 of 19, more preferred 16 of 19, more preferred 17 of 19, or even more preferred 18 of 19 amino acids, and c. the amino acid sequence of the HCDR3 is identical to SEQ ID NO: 7 in at least 8 of 11, more preferred 9 of 11, or even more preferred 10 of 11 amino acids, and d. the amino acid sequence of the LCDR1 is identical to SEQ ID NO: 8 in at least 12 of 14, or more preferred 13 of 14 amino acids, and e. the amino acid sequence of the LCDR2 is identical to SEQ ID NO: 9 in at least 4 of 7, more preferred 5 of 7, or even more preferred 6 of 7 amino acids, and f. the amino acid sequence of the LCR3 is identical to SEQ ID NO: 10 in at least 11 of 12 amino acids.

DNA Molecules of the Invention

The present invention also relates to the DNA molecules that encode an antibody of the invention. These sequences include, but are not limited to, those DNA molecules set forth in SEQ ID NOs 3 and 4.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see Sambrook et al., 1989 [Sambrook, J., Fritsch, E. F. and Maniatis, T. (1989) Molecular Cloning: A laboratory manual, Cold Spring Harbor Laboratory Press, Cold Spring Harbor, USA)] and Ausubel et al., 1995 [Ausubel, F. M., Brent, R., Kingston, R. E., Moore, D.

D., Sedman, J. G., Smith, J. A., & Struhl, K. eds. (1995). Current Protocols in Molecular Biology. New York: John Wiley and Sons].

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m=69.3+0.41(G+C)\%$
b. The $T_m$ of a duplex DNA decreases by 1° C. with every increase of 1% in the number of mismatched base pairs.
c. $(T_m)_{\mu 2}-(T_m)_{\mu 1}=18.5 \log_{10} \mu 2/\mu 1$
where µ1 and µ2 are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA [see Ausubel et al., section 2.9, supplement 27 (1994)]. Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about 0.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, subject of the present invention is an isolated nucleic acid sequence that encodes the antibody and antigen-binding fragments of the present invention.

Another embodiment of the present invention is the aforementioned isolated nucleic acid sequence, which encodes the antibodies of the present invention, whereby the nucleic acid sequences are as given in table 5.

Accordingly, the present invention includes nucleic acid molecules that hybridize to the molecules of set forth in Table 5 under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) sequence identity with one of the DNA molecules described herein. The molecules block prolactin receptor mediated signalling.

Functionally Equivalent Variants

Yet another class of DNA variants within the scope of the invention may be described with reference to the product they encode. These functionally equivalent genes are characterized by the fact that they encode the same peptide sequences found in SEQ ID No: 1 and 2 due to the degeneracy of the genetic code.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra. Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel at al., supra, chapter 8. Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention. The recombinant constructs of the present invention are used in connection with a vector, such as a plasmid, phagemid, phage or viral vector, into which a DNA molecule encoding an antibody of the invention is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. The expert in the field is able to fuse DNA encoding the variable domains with gene fragments encoding constant regions of various human IgG isotypes or derivatives thereof, either mutated or non-mutated. He is able to apply recombinant DNA technology in order to fuse both variable domains in a single chain format using linkers such as a fifteen-amino acid stretch containing three times glycine-glycine-glycine-glycine-serine. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell, and may be a prokaryotic cell, such as a bacterial cell. Introduction of the recombinant construct into the host cell can be effected by calcium phosphate transfection. DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therefore an object of the present invention is an expression vector comprising a nucleic acid sequence encoding for the novel antibodies of the present invention.

Mammalian Expression & Purification

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski. U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and U.S. Pat. No. 5,179,017, by Axel et al.). Suitable selectable markers include genes that confer resistance to drugs such as G418, hygromycin or methotrexate, on a host cell into which the vector has been introduced. For example, the dihydrofolate reductase (DHFR) gene confers resistance to methotrexate and the neo gene confers resistance to G418.

Transfection of the expression vector into a host cell can be carried out using standard techniques such as electroporation, calcium-phosphate precipitation, and DEAE-dextran transfection.

Suitable mammalian host cells for expressing the antibodies, antigen binding portions, or derivatives thereof provided herein include Chinese Hamster Ovary (CHO cells) [including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-6211 NSO myeloma cells, COS cells and SP2 cells. In some embodiments, the expression vector is designed such that the expressed protein is secreted into the culture medium in which the host cells are grown. The antibodies, antigen binding portions, or derivatives thereof can be recovered from the culture medium using standard protein purification methods.

Antibodies of the invention or an antigen-binding fragment thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragment thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

Therefore an object of the present invention are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another object of the present invention is a method of using the host cell to produce an antibody and antigen binding fragments, comprising culturing the host cell under suitable conditions and recovering said antibody.

Therefore another object of the present invention is the antibody as described in the present invention produced with the host cells of the present invention and purified to at least 95% homogeneity by weight.

Endometriosis and Adenomyosis (Endometriosis Interna)

Endometriosis is a benign, estrogen-dependent, gynecological disorder that is characterized by the presence of endometrial tissue (glands and stroma) outside the uterine cavity. Endometriotic lesions are mainly found on the pelvic peritoneum, in the ovaries and the rectovaginal septum (Obstet. Gynecol. Clin. North. Am. 24:235-238, 1997). Endometriosis is often associated with infertility and pain symptoms such as dysmenorrhoea. In addition, many patients suffer from autoimmune diseases (Hum. Reprod. 17(19): 2715-2724, 2002). Adenomyosis uteri also known as endometriosis interna describes a subform of endometriosis which is restricted to the uterus. In case of adenomyosis uteri, endometrial glands invade the myometrium and the uterine wall. According to the transplantation theory, endometrial fragments are flushed by retrograde menstruation into the peritoneal cavity in both, patients and healthy women (Obstet. Gynecol. 64:151-154, 1984). Four main factors seem to be critically involved in the successful establishment of endometriotic lesions in the pelvic cavity of patients:
  a) In the late secretory phase of the menstrual cycle, endometrial cells in healthy women become apoptotic. In patients, the extent of apoptosis in endometrial cells is clearly reduced (Fertil. Steril. 69:1042-1047, 1998). Therefore, in patients there is a higher probability than in healthy women, that endometrial fragments that have been flushed into the peritoneal cavity by retrograde menstruation do not die and implant successfully.
  b) For successful implantation in the peritoneum and long-term survival of the ectopic endometrial fragments, new blood vessels have to form (British Journal of Pharmacology, 149:133-135, 2006).
  c) Many patients suffer from autoimmune disease and thus have a compromised immune system (Hum. Reprod. 17(19): 2002, 2715-2724, 2002). This may lead to the conclusion that an intact immune response—as it is present in healthy women—may play a role for the prevention of the establishment of endometriotic lesions.
  d) Lesions have to grow and thus depend on the presence of mitogenic stimuli and growth factors.

For the treatment of endometriosis, the following approaches exist currently:
  a) Gonadotropin-releasing hormone (GnRH) analogues: lead to suppression of ovarian estradiol synthesis and induce atrophy of ectopic endometriotic implants that depend critically on the presence of estradiol for growth.
  b) Aromatase inhibitors: inhibit the local production of estradiol by endometriotic implants, induce apoptosis and inhibit proliferation of ectopic endometriotic fragments.
  c) Selective estrogen receptor modulators: have estrogen receptor antagonistic activity in normal endometrial and ectopic implants and thus lead to atrophy of implanted ectopic endometriotic tissue.
  d) Progesterone receptor agonists: inhibit proliferation of normal and ectopic endometrial cells, induce differentiation and apoptosis.
  e) Combined oral contraceptives: maintain the status quo, prevent progression of the disease, and induce atrophy of the ectopic and eutopic endometrium.
  f) Surgical excision of lesions.

GnRH analogues, SERMs, and aromatase inhibitors have severe side effects and lead to hot flushes and bone loss in young women suffering from endometriosis. Treatment with progesterone receptor agonists leads to ovulation inhibition, irregular menstrual bleeding followed by amenorrhoea, body weight gain and depression. Due to increased risk for venous thrombembolism, combined oral contraceptives are not indicated in women older than 35 years, smokers and individuals suffering from overweight. Surgical excision of lesions is prone to high recurrence rates.

The antibody of the present invention interferes with PRLR-mediated signalling stimulated by pituitary- and locally-produced prolactin or due to activating PRLR mutations and are therefore more effective than dopamine-2-receptor agonists which interfere only with pituitary prolactin secretion.

Therefore an object of the present invention is the antibody or antigen-binding fragments as described in the present invention as a medicament.

PRL and the PRLR are expressed in the uterus and play a role in normal uterine physiology; PRL can act as a potent mitogen and has an immunomodulatory role. In the present invention it is shown that alterations in the PRL/PRLR system play a role in human endometriosis. An analysis of the expression of PRL and the PRLR in endometrium of healthy women and in endometrium and lesions of patients (see Example 4) by quantitative Taqman PCR is shown in FIGS. 1 and 2.

As demonstrated in FIG. 1 (PRL expression) and FIG. 2 (PRLR expression), both PRL and its receptor are strongly upregulated in endometriotic lesions. These findings are surprising and in sharp contrast to a previously published study (Acta Obstet Gynecol Scand 81:5-10, 2002) which describe almost complete absence of PRLR expression in human endometriotic lesions.

The findings of the present invention generate for the first time experimental evidence that autocrine PRL signalling plays a fundamental role in the establishment, growth, and maintenance of endometriotic lesions.

The PRLR antibody Mat3 was successfully tested in an animal model of endometriosis interna, i.e. adenomyosis uteri in mice (see Example 5). Adenomyosis is characterized by infiltrative growth of endometrial glands in the myometrial layer of the endometrium. It resembles an endometriosis form restricted to the uterus—the only form of endometriosis non-menstruating species can develop.

Danazol which is effective in the clinical treatment of patients suffering from endometriosis is also effective in the treatment of adenomyosis uteri (Life Sciences 51:1119-1125, 1992). However danazol is an androgenic progestin and leads to severe androgenic side-effects in young women, which limits its use.

The antibody of the present invention solves the problem for providing new treatments or prevention for endometriosis and exhibit lesser side effects than current standard therapies.

Another aspect of the present invention is the use of the antibody Mat3 and antigen binding fragments as described in the present invention for the treatment or prevention of endometriosis and adenomyosis (endometriosis interna).

Benign Breast Disease and Mastalgia

Benign breast disease encompasses a variety of symptoms, such as fibrocystic breast disease, fibroadenoma, mastalgia, and macrocysts. 30-50% of premenopausal women suffer from fibrocystic breast disease (Epidemiol Rev 19:310-327, 1997). Depending on the women's age, benign breast disease can present with distinct phenotypes (J Mammary Gland Biol Neoplasia 10: 325-335, 2005): during the early reproductive phases (15-25 years) when lobular development in the normal breast takes place, benign breast disease results in fibroadenomas. Single giant fibroadenomas as well as multiple adenomas are observed. These fibroadenomas are composed of stromal as well as epithelial cells and arise from lobules. In the mature reproductive phase (25-40 years) the breast is subject to cyclical changes during each menstrual cycle. Diseased women present with cyclical mastalgia and several nodules in their breast. Later (35-55 years of age), the normal breast involutes whereas in the diseased breast macrocysts and epithelial hyperplasia with and without atypia can be observed. Those forms of benign breast disease that are accompanied by enhanced epithelial cell proliferation have a higher risk for developing mammary carcinomas. This risk can be up to 11% if cellular atypias are present in the proliferating cell fraction (Zentralbl Gynäkol 119: 54-58, 1997). 25% of women aged 60-80 years also suffer from benign breast disease, often estrogen replacement therapy or adiposity are the reasons for persisting benign breast disease after menopause (Am J Obstet Gynecol 154: 161-179, 1986).

The pathophysiology of fibrocystic breast disease is determined by estrogen predominance and progesterone deficiency that results in hyperproliferation of connective tissues (fibrosis) which is followed by facultative epithelial cell proliferation. As already mentioned, the risk of breast cancer is elevated in patients exhibiting enhanced epithelial cell proliferation within the fibrocystic foci. Clinically fibrocystic breast disease presents with breast pain and breast tenderness. 70% of the patients with fibrocystic breast disease suffer from either corpus luteum insufficiency or anovulation (Am J Obstet 154: 161-179, 1986). Corpus luteum insufficiency results in reduced progesterone levels and estrogen predominance.

Mastalgia (breast pain) affects about 70% of women at some time in their reproductive lifespan. Breast pain may or may not be associated with other criteria of the premenstrual syndrome. It has been demonstrated that women suffering from mastalgia respond with an excess prolactin release after stimulation of the hypothalamic pituitary axis (Clin Endocrinol 23: 699-704, 1985).

Standard therapies of benign breast disease and mastalgia are:
1) Bromocriptine

Bromocriptine as a dopamin agonist blocks only pituitary prolactin synthesis, but not local synthesis of prolactin in the mammary epithelial cells. It is therefore only effective in those forms of mastalgia and benign breast disease that rely on elevated systemic prolactin levels. Major side effects of bromocriptine are:
Nausea, vomiting, edema, hypotension, dizziness, hair loss, headache, and halluzinations 2) Danazol Danazol is an androgenic progestin that via its antigonadotrophic activity counteracts the estrogen predominance observed in benign breast disease. Major side effects are: Menstrual irregularities, depression, acne, hirsutism, voice deepening, and hot flushes as well as weight gain.

3) Tamoxifen

Tamoxifen is a selective estrogen receptor modulator with antiestrogenic activity in the breast and estrogenic activity in the uterus. Major side effects are:
postmenopausal symptoms such as bone loss and hot flushes, ovarial cysts, and endometrial carcinoma.

4) Progestins

Progestins inhibit benign breast disease via suppression of the pituitary gonadal axis, ovulation inhibition and estrogen depletion. Estrogen depletion leads to menopausal symptoms such as bone loss and hot flushes.

5) Low Dose Combined Oral Contraceptives

This treatment is not indicated in women older than 35 years of age, smoking as well as diabetic and overweight patients.

In general, prolactin levels have been found to be increased in one third of women with benign breast disease. Since estrogens enhance pituitary prolactin secretion, the increase in serum prolactin levels has been thought to be a consequence of the predominance of estrogens in this disease. It has been reported that an activating PRLR mutation is often present in women suffering from multiple breast adenomas—resembling a subtype of fibrocystic breast disease (Paul Kelly, Breast Congress Turin, 2007 and Proc Natl Acad Sci 105: 14533-14538; 2008).

Benign breast disease, mastalgia and premenstrual breast tension rely on one common pathophysiological mechanism: enhanced prolactin signalling. Elevated prolactin signalling can be the consequence of:
systemic hyperprolactinemia (due to pituitary adenoma)
local hyperprolactinemia (due to prolactin synthesis in proliferating mammary gland epithelial cells). Local hyperprolactinemia does not translate into elevated prolactin levels in the blood.
constitutively active PRLR signalling in the presence of normal prolactin levels (due to an activating PRLR mutation).

Given that certain forms of benign breast disease can give rise to breast cancer there is a medical need for the treatment of this disease.

To demonstrate the efficacy of neutralizing PRLR antibody Mat3 in a preclinical model of benign breast disease, a mouse model based on systemic hyperprolactinemia was employed. Adult Balb/c mice were transplanted with pituitary isografts under the kidney capsule as described in Example 6 (In: Methods in Mammary gland Biology and Breast Cancer Research, 101-107, 2000). In the mouse model of the present invention for benign breast disease, a carcinogen such as DMBA has not been used; the mice were only grafted with pituitary glands in order to study the consequence of Mat3 antibody application on enhanced benign epithelial cell proliferation. In a former study the pituitary-isografted animals were treated in addition with the carcinogen DMBA and the effects of a different monoclonal PRLR antibody on breast cancer development (Am J Pathol 133:589-595, 1988) were analysed. These antibodies were effective in treating breast cancer, the effects on benign breast disease however were not analysed (Am J Pathol 133:589-595, 1988).

In the model of the present invention, systemic hyperprolactinemia caused enhanced epithelial cell proliferation in the mammary gland, and stimulated sidebranching and lobuloalveolar development in comparison to untreated virgin control mice. As described in Example 6, the neutralizing PRLR antibody Mat3 was tested in this Balb/c mouse model in comparison to an unspecific antibody with regard to its ability to:
block sidebranching and lobuloalveolar development
inhibit mammary epithelial cell proliferation
inhibit expression of the prolactin target gene elf5

The neutralizing PRLR antibody Mat3 inhibited sidebranching (FIG. 3A) and expression of the prolactin target gene elf5 (FIG. 3B).

Another aspect of the present invention is the use of the antibody Mat3 and antigen binding fragments as described in the present invention for treatment of benign breast disease and mastalgia in pre- and postmenopausal women.

Other indications which benefit from the blockade of PRLR-mediated signalling by the antibody Mat3:
Non-Hormonal Female Contraception:
Current approaches for female contraception are the following:
a) Combined oral contraceptives containing estrogens and progestins. The progestogenic component mediates the contraceptive effect via negative feedback on the hypothalamic-pituitary-gonadal axis. The estrogenic component guarantees a good bleeding control and potentiates the gestagenic action via induction of the progesterone receptor in target cells.

b) Intrauterine devices containing progestins only.

The locally released progestin renders the endometrium in an implantation-resistant state. In addition, the cervical mucos becomes almost impermeable for sperm cells.

c) Progestin only pills and implants.

The progestin inhibits ovulation via negative feedback on the hypothalamic-pituitary-gonadal axis. In addition the permeability of the cervical mucus for sperm cells is reduced.

d) Vaginal rings containing ethinylestradiol plus progestins

The main side-effect of combined oral contraceptives is the elevated risk for venous thromboembolism (VTE). Moreover, overweight or smoking women, as well as women suffering from autoimmune diseases such as lupus and women older than 35 years cannot use oral combined contraceptives.

Intrauterine devices and implants containing progestins only can lead to dysfunctional uterine bleeding.

Progestin only pills can cause irregular bleeding patterns, spotting, amenorrhea. The risk for ectopic pregnancies increases. Weight gain and reductions in bone mass density are further side effects.

Vaginal rings can lead to vaginitis, leukorrhea or expulsion.

PRLR-deficient mice have been generated a few years ago (Genes Dev 11:167-178, 1997). Interestingly, PRLR-deficient females, but not male mice, are completely sterile. PRLR$^{-/-}$ females exhibited an arrest of egg development immediately after fertilization, i.e. they showed an arrest of preimplantation development whereas ovulation was normal. Only very few oocytes reached the blastocyst stage and were unable to implant in mutant females but developed to normal embryos in wildtype foster mothers after transplantation. The infertility phenotype of PRLR-deficient mice could be rescued until midterm pregnancy by progesterone supplementation. Obviously. PRLR-mediated signalling plays an important role in the maintenance and function of the corpus luteum producing progesterone that is necessary to allow and maintain pregnancy. In addition PRLR-deficient females, but not males, exhibited a reduction in body weight associated with a reduction in abdominal fat mass and leptin levels.

So far, no inactivating human PRLR mutation is known, therefore the precise role of PRLR-mediated signalling in human fertility is still unknown. However, there is increasing evidence that also in humans; a minimal prolactin level is required to allow for successful pregnancy. Patients suffering from primary infertility due to hyperprolactinemic corpus luteum insufficiency were treated with bromocriptin. In some cases, prolactin levels were oversuppressed and shortened luteal phases reappeared again (Bohnet H G et al. in Lisuride and other dopamine agonists edited by D. B. Calne et al, Raven Press, New York, 1983). From these data it was concluded that hyper- and hypoprolactinemic states interfere negatively with female fertility. This can be explained by the interaction of PRL with its receptor. In case of low prolactin levels, there is no sufficient receptor activation, whereas in case of hyperprolactinemia, there is also no sufficient receptor activation, since all receptors are blocked by one prolactin molecule and cannot dimerize anymore. In other words, the dose response for prolactin is bell-shaped and optimal receptor activation is achieved only in a certain concentration range. There is evidence from a second study that lack of endometrial prolactin expression in patients leads to early implantation failure (Human Reprod. 19:1911-1916, 2004).

Moreover, it has been shown that ex vivo, prolactin can prevent apoptosis of cultured human granulosa cells and thus maintains early corpus luteum function as it has been demonstrated in PRLR-deficient mice (Human Reprod. 18:2672-2677, 2003).

Compared to the aforementioned standard approaches, female contraception with neutralizing PRLR antibodies has several advantages:

the antibodies can be used in smoking, overweight, and older women as well as in women suffering from lupus erythematodes (PRLR antibodies might even be beneficial for the treatment of lupus and the reduction of abdominal fat, i.e. PRLR-deficient mice had less abdominal fat).

the PRLR antibodies do not elevate the VTE (venous thrombembolic) risk in contrast to estrogens and progestins used in combined oral contraception, neutralization of PRLR-mediated signalling leads to inhibition of breast epithelial proliferation and in contrast to hormonal approaches for fertility control might even protect users from breast cancer.

Another object of the present invention is the use of the antibody Mat3 for female contraception with reduced side effects compared to standard treatments.

Lactation Inhibition

Prolactin is the main hormone involved in lactation after child birth. This is evidenced by the phenotype of PRLR-deficient mice. Even heterozygous mice have severe lactational problems and are completely unable to nurse their offspring (Frontiers in Neuroendocrinology 22:140-145, 2001).

For many reasons, women have to stop breast feeding, i.e. maternal intake of drugs potentially dangerous to the infant, serious infections (mastitis, nephritis), profuse postpartum hemorrhage, and severe maternal diseases such as diabetes, carcinoma, and debility or diseases of the newborn. Currently, dopamine receptor agonists such as bromocriptine and lisuride are used to inhibit lactation after child birth. However, these compounds can provoke severe side effects such as nausea, vomiting, edema, hypotension, dizziness, hair loss, headache, and halluzinations. In addition dopamine receptor agonists are not indicated in women suffering from cardiovascular disease and hypertension. A further disadvantage of bromocriptine is its short half life time requiring drug intake 4-6 times daily over a period of 14 days.

Therefore, we expect that neutralising PRLR antibodies are suitable for lactation inhibition. In a former publication an antiserum generated against partly purified PRLR was given to lactating rats. It was speculated that the antiserum led to lactation inhibition since there was a small decrease in litter weight (Endocrinology 102:1657-1661, 1978). However the authors were not able to exclude that even other mechanisms might have led to the slight reduction in litter weight. In addition they observed that the antiserum caused an increase in corpora lutea in treated rats ((Endocrinology 102:1657-1661, 1978). This observation is in clear contrast to the phenotype of PRLR-deficient mice ((Genes Dev 11:167-178, 1997) in which ovulation was unimpaired and in which no increase in corpora lutea was observed. Most likely the employed antiserum blocked some additional unknown molecules.

Another object of the present invention is the use of the antibody Mat3 for inhibition of lactation.

Benign Prostate Hyperplasia

Benign prostate hyperplasia (BPH) is the fourth most prevalent healthcare condition in older men. Prostate enlargement is an age-dependent progressive condition that affects more than 50% of men aged ≥50 years of age. BPH is characterized by hyperplasia of prostatic stromal and epithelial cells, resulting in the formation of large discrete nodules in the periurethral region of the prostate which compresses the urethral canal. Thus, impairment of urine flow is one major consequence of BPH.

Standard therapies for BPH encompass:
a) α1-adrenergic receptor antagonists (e.g. tamsulosin, alfuzosin, terazosin, doxazosin) relief the BPH symptoms in the lower urinary tract. They decrease bladder outlet obstruction by blocking alpha-receptor-mediated stimulation of prostate smooth muscle. Major side-effects are vasodilatory adverse events, dizziness and ejaculation failure.
b) 5α-reductase inhibitors (e.g. finasteride)
   5α-reductase inhibitors prevent the formation of dihydrotestosterone, the active form of testosterone in the prostate, which is responsible for the enlargement of the prostate. Major side-effects are sexual dysfunction, such as erectile disorders and decreased libido.
c) Transurethral resection of the prostate (TURP)
   This surgical treatment is associated with high morbidity. Side-effects are bleeding, incontinence, stricture formation, loss of ejaculation, and bladder perforation.
d) Prostate stenting
   A stent is inserted into the prostatic part of the urethra to guarantee proper urine flow. Major side-effects are encrustation, urinary tract infection, and migration of the stent. Moreover, stents have to be removed before any transurethral manipulation.

As described for the mammary gland, PRL and the PRLR act in an autocrine/paracrine way (J. Clin. Invest. 99:618 pp, 1997) within the prostate.

Clinical studies indicate that hyperprolactinemia (and agromegaly) is associated with prostatic enlargement and stromal accumulation of inflammatory cells. Human growth hormone can bind to the human PRLR in the presence of zinc which might explain why acromegaly can lead to benign prostate hyperplasia. PRL serum levels are often elevated in patients with BPH.

Transgenic animals overexpressing the PRL gene ubiquitously, develop severe stromal prostate hyperplasia, indicating PRL as an important pathophysiological factor for the development of prostate hyperplasia (Endocrinology 138: 4410 pp, 1997). Furthermore, local overexpression of PRL in transgenic mice under the prostate specific probasin promoter results in stromal expansion, accumulation of inflammatory cells and focal epithelial dysplasia which are basic characteristics of human BPH (Endocrinology 144:2269 pp, 2003).

Another aspect of the present invention is the use of the antibody Mat3 or antigen-binding fragments as described in the present invention for treatment of benign prostate hyperplasia.

Combined Hormone Therapy

For the treatment of hot flushes in postmenopausal women still having a uterus, combinations of estrogen (estradiol, or conjugated equine estrogens=CEE) and progestins (for example medroxyprogesterone acetate (MPA), progesterone, drospirenone, levonorgestrel) were used. Progestins have to be added to inhibit estradiol-activated uterine epithelial cell proliferation. However, addition of progestins increases mammary epithelial cell proliferation. Since both, normal as well as cancerous mammary epithelial cells respond with proliferation towards combined estrogen plus progestin treatment, the relative risk of breast cancer was found to be increased after CEE plus MPA treatment (JAMA 233:321-333; 2002).

The antibody of the present invention solves the problem for treating enhanced breast epithelial cell proliferation observed under combined hormone therapy.

Another object of the present invention is the use of neutralizing PRLR antibody Mat3 or antigen-binding fragments in combined hormone therapy (i.e. estrogen+progestin therapy) to inhibit mammary epithelial cell proliferation.

Hair Loss

Treatment of hair loss is still an unmet need. Scalp hair growth in cycles: the anagen phase is characterized by active hair growth; the catagen phase shows involution and is followed by the telogen phase (resting). The exogen phase (the release of the dead hair) coincides with the end of the telogen phase. Hair loss can be the consequence of disturbed hair growth in any phase.

Telogen hair loss can have many triggers (physiological and emotional stress, medical conditions, iron and zinc deficiency), importantly androgenic alopecia in its early stages shows telogen hair shedding (Cleveland clinic journal of medicine 2009; 76:361-367). Anagen hair loss is often the consequence of radiation or chemotherapy.

Minoxidil and Finasteride are used for the treatment of androgenetic hair loss, whereas glucocorticoids are used for alopecia greata. In general, all of these treatments have side-effects (finasteride: libido loss and impotence in men, glucocorticoids: diabetes, weight gain, osteoporosis), and the problem of treating hair loss has not been completely solved.

In rodents, shaving experiments in adult animals were used to analyze the effect of compounds on hair loss by using hair regrowth in the shaved area as readout paradigm (British Journal of dermatology 2008; 159:300-305). Shaving of adult animals (hair mostly in telogen phase) induces the anagen phase that is charactzerized by hair growth.

Prolactin and the PRLR have been found to be expressed in hair follicles. From the expression data it was suggested that interference with PRLR-mediated signalling might be useful against hair loss, but no functional data were shown to prove this hypothesis (Aktuelle Dermatologie 31:109-116, 2005).

The antibody of the present invention solves the problem for providing new treatments for hyper- and normoprolactinemic hair loss in women and men.

Therefore a further aspect of the present invention is to employ the antibody Mat3 or antigen-binding fragments for the treatment or prevention of hyper- and normoprolactinemic hair loss.

Treatment and Prevention of Antiestrogen-Resistant Breast Cancer

It has been suggested that the PRLR is overexpressed in human breast cancer (J Clin Endocrinol Metab 83:667-674, 1998) and that negative interference with the PRL-PRLR interaction might have positive impact on breast cancer treatment (Int. J. Cancer: 55(5): 712-721, 1993). There is evidence, that in general, plasma prolactin levels correlate with breast cancer risk (Cancer Lett 243:160-169, 2006). In patients with tamoxifen-resistant breast cancer, the development of progressive disease correlates with prolactin plasma levels (Eur J Surg Oncol 20:118-121, 1994). Transgenic mice overexpressing prolactin are more prone to the development of breast cancer (J Clin Invest 100:2744-2751, 1997).

Another aspect of the present invention is the use of the antibody Mat3 or antigen-binding fragments as described in the present invention for treatment or prevention of antiestrogen-resistant breast cancer.

DEFINITIONS

The target antigen human "PRLR" as used herein refers to a human polypeptide having substantially the same amino acid sequence in its extracellular domain as the amino acid positions 1 to 210 of SEQ ID NO. 12 and naturally occurring allelic and/or splice variants thereof. "ECD of PRLR" as used herein refers to the extracellular portion of PRLR represented by the aforementioned amino acids. In addition the target human PRLR also encompasses mutated versions of the receptor, such as the activating mutation I146L described by Paul Kelly (Proc Natl Acad Sci USA. 105 (38): 14533-14538, 2008; and oral communication Turin, 2007).

The target antigen monkey "PRLR" as used herein refers to a rhesus as well as cynomolgus polypeptide having substantially the same amino acid sequence in its extracellular domain as the amino acid positions 1 to 210 of SEQ ID NO. 11 and naturally occurring allelic and/or splice variants thereof. "ECD of PRLR" as used herein refers to the extracellular portion of PRLR represented by the aforementioned amino acids.

The target antigen murine or mouse "PRLR" as used herein refers to a murine polypeptide having substantially the same amino acid sequence in its extracellular domain as the amino acid positions 1 to 210 of SEQ ID NO. 13 and naturally occurring allelic and/or splice variants thereof. "ECD of PRLR" as used herein refers to the extracellular portion of PRLR represented by the aforementioned amino acids.

As used herein, the phrase "therapeutically effective amount" is meant to refer to an amount of therapeutic or prophylactic antibody that would be appropriate to elicit the desired therapeutic or prophylactic effect or response, including alleviating some or all of such symptoms of disease or reducing the predisposition to the disease, when administered in accordance with the desired treatment regimen.

As used herein, an antibody "binds specifically to," is "specific to/for" or "specifically recognizes" an antigen (here, PRLR) if such an antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. However, "specific binding" also may refer to the ability of an antibody to discriminate between the target antigen and one or more closely related antigen(s), which are used as reference points. Additionally, "specific binding" may relate to the ability of an antibody to discriminate between different parts of its target antigen, e.g. different domains, subdomains or regions of PRLR, such as epitopes in the N-terminal or in the C-terminal region of the ECD of PRLR, or between one or more key amino acid residues or stretches of amino acid residues of the ECD of PRLR.

"Affinity" or "binding affinity" $K_D$ are often determined by measurement of the equilibrium association constant (ka) and equilibrium dissociation constant (kd) and calculating the quotient of kd to ka ($K_D$=kd/ka). The term "immunospecific" or "specifically binding" means, that the antibody binds to PRLR or its ECD with an affinity $K_D$ of lower than or equal to $10^{-6}$M (monovalent affinity). The term "high affinity" means, that the antibody binds to PRLR or its ECD with an affinity ($K_D$) of lower than or equal to $10^{-7}$M (monovalent affinity). The antibody may have substantially greater affinity for the target antigen compared to other unrelated molecules. The antibody may also have substantially greater affinity for the target antigen compared to homologs, e.g. at least 1.5-fold, 2-fold, 5-fold 10-fold, 100-fold, $10^{-3}$-fold, $10^{-4}$-fold, $10^{-5}$-fold, $10^{-6}$-fold or greater relative affinity for the target antigen. Such affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51: 660 (1949).

As used herein the phrase "antibodies antagonize prolactin mediated signalling" is meant to refer to a blockade of prolactin receptor activation by the antibodies of the present invention which leads to a complete inhibition of prolactin receptor mediated signalling.

As used herein the phrase "antibodies compete for binding" is meant to refer to a competition between one antibody and a second ligand for binding to the prolactin receptor.

The term "antibody" is used in the broadest sense and includes fully assembled antibodies, monoclonal antibodies, polyclonal antibodies, multispecific antibodies (e.g., bispecific antibodies), antibody fragments that can bind the antigen (e.g., Fab', F'(ab)2, Fv, single chain antibodies, diabodies), camel bodies and recombinant peptides comprising the forgoing as long as they exhibit the desired biological activity. Antibodies may carry different constant domains (Fc domains) on their heavy chain preferably derived from IgG1. IgG2, or IgG4 isotypes (see below). Mutations for modification of effector functions may be introduced. Amino acid residues in the Fc-domain that play a dominant role in the interactions with the complement protein C1q and the Fc receptors have been identified and mutations influencing effector functions have been described (for a review see Labrijn at al., Current opinion in Immunology 20: 479-485, 2008). Particularly, aglycosylation of IgG1 may be achieved by mutating asparagine to alanine or asparagine to glutamine at amino acid position 297, which has been reported to abolish antibody-derived cell-mediated cytotoxicity (ADCC) (Sazinsky et al., Proc. Nat. Acad. Sci. 105 (51): 20169, 2008; Simmons et al., J. of Immunological Methods 263: 133-147, 2002). Replacement of lysine by alanine at position 322 leads to reduction of ADCC and removal of complement-derived cytotoxicity (CDC), while simultaneous replacement of the two leucines at position 234 and 235 by alanines leads to avoidance of ADCC and CDC [Hezareh et al., J. of Virology, 75 (24): 12161-12168, 2001]. In order to apply IgG4 isotypes as bivalent therapeutics in vivo which retain avidity, a modification such as the serine-to-proline exchange in the 'core hinge region' (Schuurman. J. et al. Immunology 97: 693-698, 1999) may be introduced. The tendency of human IgG2 molecules to form heterogeneous covalent dimers may be circumvented by exchanging one of the cysteines at position 127, 232 and 233 to serine (Allen et al., Biochemistry, 2009, 48 (17), pp 3755-3766). An alternative format with reduced effector function may be the IgG2m4 format, derived from IgG2 carrying four IgG4-specific amino acid residue changes (An at al., mAbs 1(6), 2009). Antibody fragments may be produced by recombinant DNA techniques or by enzymatic or chemical cleavage of intact antibodies and are described further below. Nonlimiting examples of monoclonal antibodies include murine, chimeric, humanized, human, and Human Engineered™ immunoglobulins, antibodies, chimeric fusion proteins having sequences derived from immunoglobulins, or muteins or derivatives thereof, each described further below. Multimers or aggregates of intact molecules and/or fragments, including chemically derivatized antibodies, are contemplated.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used may be made by the hybridoma method first described by Kohler et al., Nature, 256: 495 [1975, or may be made by recombinant DNA methods (see, e.g., U.S. Pat. No. 4,816, 567). The "monoclonal antibodies" may also be recombinant, chimeric, humanized, human, Human Engineered™, or antibody fragments, for example.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes often have ADCC activity. Human light chains are classified as kappa (K) and lambda (A) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

A "functional fragment" or "antigen-binding antibody fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody. i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains [amino acid positions 1 to 109 of VL and 1 to 113 of VH, while numbering of amino acid positions occurs according to the Kabat database (Johnson and Wu, Nucleic Acids Res., 2000, 28, 214-218)]. A preferred class of immunoglobulins for use in the present invention is IgG.

The term "hypervariable" region refers to the amino acid residues of the variable domains VH and VL of an antibody or functional fragment which are responsible for antigen-binding. The hypervariable region comprises amino acid residues from a "complementarity determining region" or CDR [i.e., residues 24-34 (LCDR1), 50-56 (LCDR2) and 88-97 (LCDR3) in the light chain variable domain and 29-36 (HCDR1), 48-66 (HCDR2) and 93-102 (HCDR3) in the heavy chain variable domain as described in FIG. 12] and/or those residues from a hypervariable loop [i.e., residues 26-32 (within LCDR1), 50-52 (within LCDR2) and 91-96 (within LCDR3) in the light chain variable domain and 26-32 (within HCDR1), 53-55 (within HCDR2) and 96-101 (within HCDR3) in the heavy chain variable domain as described by Chothia et al., J. Mol. Biol. 196: 901-917 (1987)].

Nonlimiting examples of antibody fragments include Fab, Fab', F(ab')2, Fv, domain antibody (dAb), complementarity determining region (CDR) fragments, single-chain antibodies (scFv), single chain antibody fragments, diabodies, triabodies, tetrabodies, minibodies, linear antibodies (Zapata at al., Protein Eng., 8 (10): 1057-1062 (1995)); chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity; and multispecific antibodies formed from antibody fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag). An antibody other than a "bispecific" or "bifunctional" antibody is understood to have each of its binding sites identical. The F(ab')$_2$ or Fab may be engineered to minimize or completely remove the intermolecular disulphide interactions that occur between the $C_{H1}$ and $C_L$ domains. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two "Fv" fragments. An "Fv" fragment is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen.

"Single-chain Fv" or "sFv" or "scFv" antibody fragments comprise the VH and VL domains of antibody, wherein these domains are present in a single polypeptide chain. Preferably, the Fv polypeptide further comprises a polypeptide linker between the VH and VL domains that enables the Fv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain ($CH_1$) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them.

"Framework" or FR residues are those variable domain residues other than the hypervariable region residues.

The phrase "constant region" refers to the portion of the antibody molecule that confers effector functions.

The term "mutein" or "variant" can be used interchangeably and refers to the polypeptide sequence of an antibody that contains at least one amino acid substitution, deletion, or insertion in the variable region or the portion equivalent to the variable region, provided that the mutein or variant retains the desired binding affinity or biological activity.

Muteins may be substantially homologous or substantially identical to the parent antibody.

The term "derivative" refers to antibodies covalently modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids.

A "human" antibody or functional human antibody fragment is hereby defined as one that is not chimeric or "humanized" and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source). Examples of human antibodies include n-CoDeR-based antibodies as described by Carlsson and Söderlind Exp. Rev. Mol. Diagn. 1 (1), 102-108 (2001), Söderlin et al. Nat. Biotech. 18, 852-856 (2000) and U.S. Pat. No. 6,989,250.

A "humanized antibody" or functional humanized antibody fragment is defined herein as one that is (i) derived from a non-human source (e.g., a transgenic mouse which bears a heterologous immune system), which antibody is based on a human germline sequence; or (ii) CDR-grafted, wherein the CDRs of the variable domain are from a non-human origin, while one or more frameworks of the variable domain are of human origin and the constant domain (if any) is of human origin.

The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

"Human Engineered™" antibodies generated by altering the parent sequence according to the methods set forth in Studnicka at al., U.S. Pat. No. 5,766,886 such as the antibody represented by SEQ ID NOs 14 and 15 and described in patent application WO08/022,295.

An antibody of the invention may be derived from a recombinant antibody gene library. The development of technologies for making repertoires of recombinant human antibody genes, and the display of the encoded antibody fragments on the surface of filamentous bacteriophage, has provided a recombinant means for directly making and selecting human antibodies, which also can be applied to humanized, chimeric, murine or mutein antibodies. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function. Typically, the Fd fragment (VH-CH1) and light chain (VL-CL) of antibodies are separately cloned by PCR and recombined randomly in combinatorial phage display libraries, which can than be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and re-amplification, a procedure termed panning, Fab specific for the antigen are enriched and finally isolated.

A variety of procedures have been described for deriving human antibodies from phage-display libraries. Such libraries may be built on a single master framework, into which diverse in vivo-formed (i.e. human-derived) CDRs are allowed to recombine as described by Carlsson and Söderlind Exp. Rev. Mol. Diagn. 1 (1), 102-108 (2001), Söderlin et al. Nat. Biotech. 18, 852-856 (2000) and U.S. Pat. No. 6,989, 250. Alternatively, such an antibody library may be based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064. For a review of phage display techniques, see WO08/022,295 (Novartis).

Alternatively, an antibody of this invention may come from animals. Such an antibody may be humanized or Human Engineered summarized in WO08/022,295 (Novartis); such an antibody may come from transgenic animals [see also WO08/022,295 (Novartis)].

As used herein, different 'forms' of antigen, e.g. PRLR, are hereby defined as different protein molecules resulting from different translational and posttranslational modifications, such as, but not limited to, differences in splicing of the primary prolactin receptor transcript, differences in glycosylation, and differences in posttranslational proteolytic cleavage.

As used herein, the term 'epitope' includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to 'bind the same epitope' if one antibody is shown to compete with the second antibody in a competitive binding assay, by any of the methods well known to those of skill in the art, and all amino acids of the epitope are bound by the two antibodies.

The term 'maturated antibodies' or 'maturated antigen-binding fragments' such as maturated Fab variants includes derivatives of an antibody or antibody fragment exhibiting stronger binding—i.e. binding with increased affinity—to a given antigen such as the extracellular domain of the PRLR. Maturation is the process of identifying a small number of mutations within the six CDRs of an antibody or antibody fragment leading to this affinity increase. The maturation process is the combination of molecular biology methods for introduction of mutations into the antibody and screening for identifying the improved binders.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to block proliferation of PRLR-positive cells in a treated area of a subject either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody of the invention might be co-administered with known medicaments, and in some instances the antibody might itself be modified. For example, an antibody could be conjugated to an immunotoxin or radioisotope to potentially further increase efficacy. The inventive antibodies can be used as a therapeutic or a diagnostic tool in a variety of situations where PRLR is undesirably highly expressed. Disorders and conditions particularly suitable for treatment with an antibody of the inventions are endometriosis, adenomyosis, non-hormonal female fertility contraception, benign breast disease and mastalgia, lactation inhibition, benign prostate hyperplasia, fibroids, hyper- and normoprolactinemic hair loss, and cotreatment in combined hormone therapy to inhibit mammary epithelial cell proliferation.

To treat any of the foregoing disorders, pharmaceutical compositions for use in accordance with the present invention may be formulated in a conventional manner using one or more physiologically acceptable carriers or excipients. An antibody of the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody of the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Pharmaceutical Compositions and Administration

The present invention also relates to pharmaceutical compositions which may comprise PRLR antibodies, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished parenterally. Methods of parenteral delivery include topical, intra-arterial (directly to the tumor), intramuscular, subcutaneous, intramedullary, intrathecal, intraventricular, intravenous, intraperitoneal, intrauterine or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically. Further details on techniques for formulation and administration may be found in the latest edition of Remington's Pharmaceutical Sciences (Ed. Maack Publishing Co, Easton, Pa.).

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The parenteral administration also comprises methods of parenteral delivery which also include intra-arterial, intramuscular, subcutaneous, intramedullary, intrathecal, and intraventricular, intravenous, intraperitoneal, intrauterine, vaginal, or intranasal administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

In another embodiment, the kits may contain DNA sequences encoding the antibodies of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmids may also contain numerous other elements to facilitate cloning and expression of the encoded proteins. Such elements are well known to those of skill in the art and include, for example, selectable markers, initiation codons, termination codons, and the like.

Manufacture and Storage

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of PRLR antibodies, such labeling would include amount, frequency and method of administration.

Therapeutically Effective Dose

Pharmaceutical compositions suitable for use in the present invention include compositions wherein the active ingredients are contained in an effective amount to achieve the intended purpose, i.e. treatment of a particular disease state characterized by PRLR expression. The determination of an effective dose is well within the capability of those skilled in the art.

For any compound, the therapeutically effective dose can be estimated initially either in cell culture assays, e.g., lymphoma cells, or in animal models, usually mice, rats, rabbits, dogs, pigs or monkeys. The animal model is also used to achieve a desirable concentration range and route of administration. Such information can then be used to determine useful doses and routes for administration in humans.

A therapeutically effective dose refers to that amount of protein or its antibodies, antagonists, or inhibitors that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies are used in formulating a range of dosage for human use. The dosage of such compounds lies preferably within a range of circulating concentrations what include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, eg, size and location of endometriotic lesions; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks, or once within a month depending on half-life and clearance rate of the particular formulation.

Normal dosage amounts may vary from 0.1 to 100,000 micrograms, up to a total dose of about 2 g, depending upon the route of administration. Guidance as to particular dosages and methods of delivery is provided in the literature. See U.S. Pat. No. 4,657,760; U.S. Pat. No. 5,206,344; or U.S. Pat. No. 5,225,212. Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabeled antibody may range from 0.1 to 10 mCi/mg of protein (Riva et al., Clin. Cancer Res. 5: 3275s-3280s, 1999; Wong et al., Clin. Cancer Res. 6: 3855-3863, 2000; Wagner et al., J. Nuclear Med. 43: 267-272, 2002).

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook at al., Molecular Cloning: A Laboratory Manual, 2nd Ed.; Cold Spring Harbor Laboratory Press, Cold Spring Harbor, N.Y., 1989.

DESCRIPTION OF THE FIGURES

FIG. 1: Expression of prolactin-mRNA (PRL-mRNA) (analyzed by real-time TaqMan PCR analysis) in human endometrium and lesions (ectopic tissue) from healthy women and women suffering from endometriosis.

FIG. 2: Expression of prolactin receptor-mRNA (PRLR-mRNA) (analyzed by real-time TaqMan PCR analysis) in human endometrium and lesions (ectopic tissue) from healthy women and women suffering from endometriosis.

FIG. 3A: Neutralizing prolactin receptor antibody Mat3 inhibited sidebranching in mammary glands of mice which have been employed in a hyperprolactinemic surrogate model of benign breast disease. The unspecific antibody had no effect. Healthy normoprolactinemic mice (no pituitary) showed reduced sidebranching, whereas pituitary transplantation (hyperprolactinemia) enhanced sidebranching and lobuloalveolar development. The specific antibody Mat3 antagonized the effects of hyperprolactinemia.

FIG. 3B: The neutralizing prolactin receptor antibody Mat3 inhibited the induction of the prolactin target gene elf5 in mammary glands of mice in a hyperprolactinemic surrogate model of benign breast disease. The unspecific antibody had no effect. Healthy, normoprolactinemic mice (no pituitary) showed reduced elf 5 expression in the mammary gland, whereas pituitary transplantation (hyperprolactinemia) strongly stimulated elf 5 gene expression. The specific antibody Mat3 but not the unspecific control antibody antagonized the effects of hyperprolactinemia.

FIG. 4: Kabat Numbering of framework amino acid positions according to Johnson and Wu (Nucleic Acids Res. 2000, 28, 214-218).

FIG. 5A: FACS analysis results with the anti-PRLR antibody HE06642. Binding of the antibody was determined at a fixed concentration on HEK293 cells expressing the human and mouse PRLR in comparison to the parental cell line not expressing PRLR. Y-axis: #, Median Fluorescence Intensity at 0.37 µg/ml HE06642 as IgG1 molecule. *, 1=HEK293 with human PRLR; 2=HEK293 with murine PRLR; 3=HEK293 without PRLR.

FIG. 5B: FACS analysis results with the anti-PRLR antibody Mat3. Binding of the antibody was determined at a series of different concentrations on HEK293 cells expressing the human PRLR and Ba/F cells expressing the rhesus PRLR in comparison to a cell line (HEK293) not expressing PRLR. Maximal signal intensities at highest antibody concentrations depend on the number of PRLRs expressed on the cell surfaces, i.e. HEK293 and Ba/F cells do not carry the same number of PRLRs on their surface. Y-axis: #, Median Fluorescence Intensity; X-axis: °, different concentrations in µg/ml of the antibody Mat3 as IgG2 molecule; *, 1 (circles) =HEK293 with human PRLR; 2 (triangles)=Ba/F with rhesus monkey PRLR; 3 (squares)=HEK293 without PRLR.

FIG. 6A: Alignment of the sequence region of the Mat3-VL domain with the most similar human V segment identified in VBASE2 (Mat3-VL is 90% identical to germline sequence humIGLV056).

FIG. 6B: Alignment of the sequence region of the Mat3-VH domain with the most similar human V segment identified in VBASE2 (Mat3-VH is 90% identical to germline sequence humIGHV313).

FIG. 6C: Alignment of the sequence region of the HE06642-VL domain with the most similar human V segment identified in VBASE2 (HE06642-VL is 80% identical to germline sequence humIGKV083).

FIG. 6D: Alignment of the sequence region of the HE06642-VH domain with the most similar human V segment identified in VBASE2 (HE06642-VH is 89% identical to germline sequence humIGHV313).

Fab-containing E. coli supernatants were tested for binding to the immobilized extracellular domain of the human PRLR. The figure illustrates the binding of the Fab variants as a bar diagram. The signal intensities (extinction) are given on the y-axes (#), the names of the Fab variants (*) on the x-axes. Elevated signal intensity of the maturated Fab variant 005-004-20-2 compared to the non-maturated Fab of the parental antibody 005-004 demonstrate better PRLR-binding of 005-004-20-2 compared to 005-004. The "variant" pET28 represents a supernatant of an E. coli strain carrying the Fab-expression plasmid pET28a (Novagen, EMD Chemicals Group, Merck, Darmstadt, Germany) which does not express any Fab.

FIG. 8: Barplot representation of Pepscan ELISA results.

Each plotted value represents the average value obtained for 54 peptides with S.E.M (standard error of mean). The black bars represent the relative binding strength of antibody HE06642. The white bars represent the relative binding strength of antibody Mat3. The data was normalized to average over the entire 2916 peptide dataset and corrected for background signal.

Figure 8A:
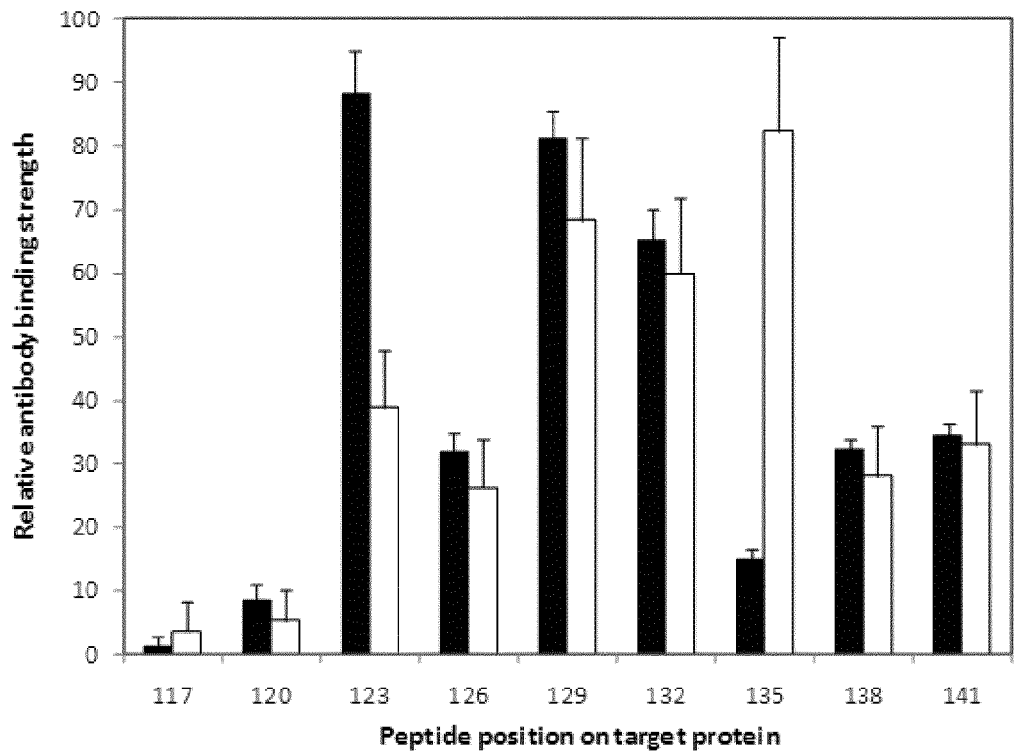

FIG. 8A shows the ELISA results for a subset of peptides ranging from amino acids 103-PDPPLELAVEVKQPE-117 indicated as '117' on the X-axis to 127-WSPPTLIDLKTG-WFT-141 (indicated as '141'). I. e. these peptides, which were shifted by three amino acids along the ECD amino acid sequence, cover the region from amino acid position 103 to 141 of the ECD of human PRLR. The strongest differences observed within this dataset are for peptide 109-LAVEVKQPEDRKPYL-123 (indicated as '123') with a significance p-value of $4 \times 10^{-12}$, and for peptide 121-PYLWIK-WSPPTLIDL-135 (indicated as '135') with a significance p-value of $7 \times 10^{-40}$.

Figure 8B:
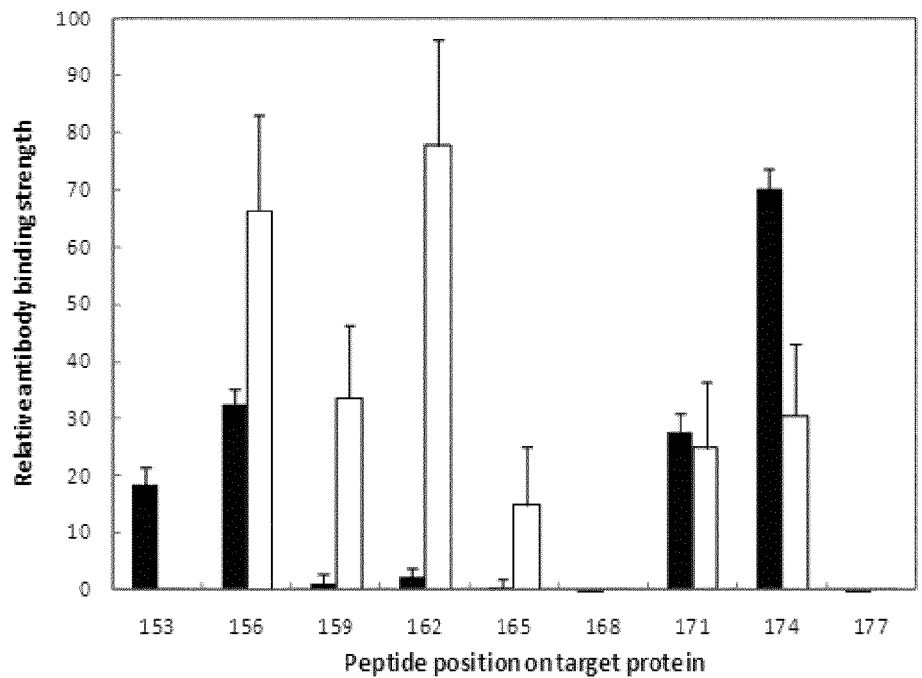

FIG. 8B shows the ELISA results for a subset of peptides ranging from 139-WFTLLYEIRLKPEKA-153 (indicated as '153' on the X-axis) to 163-QQTEFKILSLHPGQK-177 (indicated as '177'). I. e. these peptides, which were shifted by three amino acids along the ECD amino acid sequence, cover the region from amino acid position 139 to 177 of the ECD of human PRLR. The strongest differences observed within this dataset are for peptide 148-LKPEKAAEWEIHFAG-162 (indicated as '162') with a significance p-value of $6 \times 10^{-26}$, and for peptide 160-FAGQQTEFKILSLHP-174 (indicated as '174') with a significance p-value of $8 \times 10^{-8}$.

These data demonstrate that both antibodies bind to the S2 subdomain of the ECD of human PRLR (amino acid 101 to 210) and therefore are non-competitive to the natural ligand PRL which mainly binds to the S1 domain. However, this peptide scan showed that there are differences in binding to the S2 domains between Mat3 and HE06642. This finding indicates why the antibody Mat3 shows a different species-specificity and potency compared to HE06642.

Figure 9:
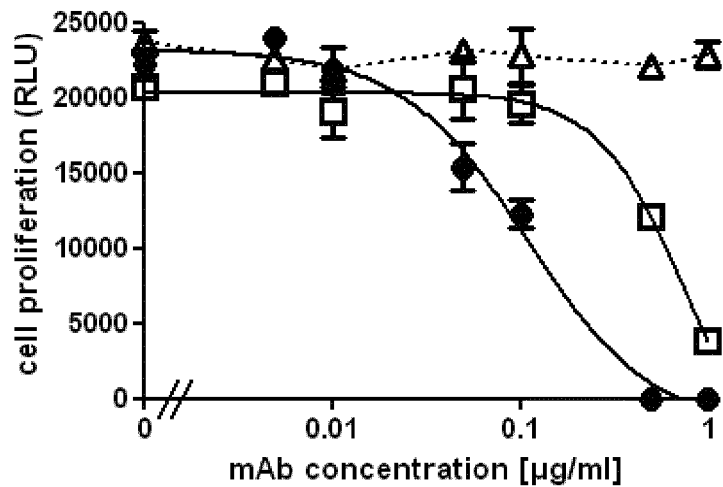

FIG. 9: Inhibition of prolactin-induced proliferation of BaF3 cells (monoclonal cells stably transfected with human prolactin receptor) by neutralizing prolactin receptor antibodies and unspecific control antibodies. The $IC_{50}$ values were determined for the following antibodies in IgG1 format: Mat3 (closed circles), $IC_{50}$=0.7 nM [100% inhibition at 1 µg/ml (=6.7 nM)]; HE06.642 (open squares), $IC_{50}$=4.2 nM [8]% inhibition at 1 µg/ml (=6.7 nM)]; unspecific control antibody (open triangles): no inhibitory effect.

Figure 10:
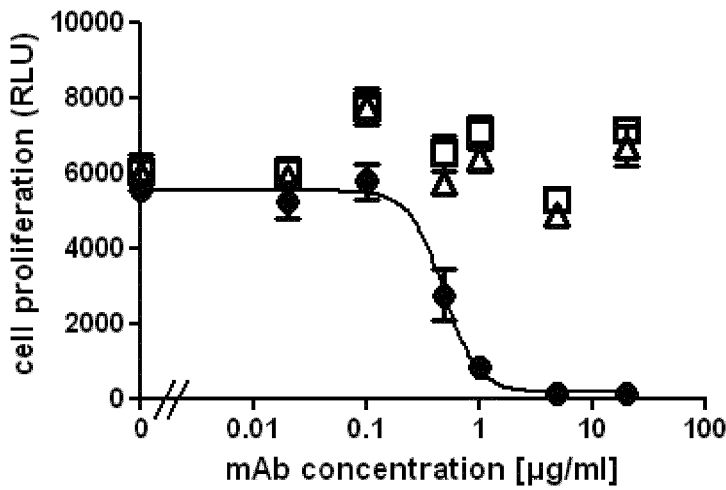

FIG. 10: Inhibition of prolactin-induced proliferation of BaF3 cells (monoclonal cells stably transfected with the murine prolactin receptor) by neutralizing prolactin receptor antibodies and unspecific control antibodies. The $IC_{50}$ values were determined for the following antibodies in IgG1 format: Mat3 (closed circles), $IC_{50}$=3.0 nM [97.4% inhibition at 1

μg/ml (=6.7 nM)]; HE06.642 (open squares), no inhibitory effect; unspecific control antibody (open triangles): no inhibitory effect.

Figure 11A:
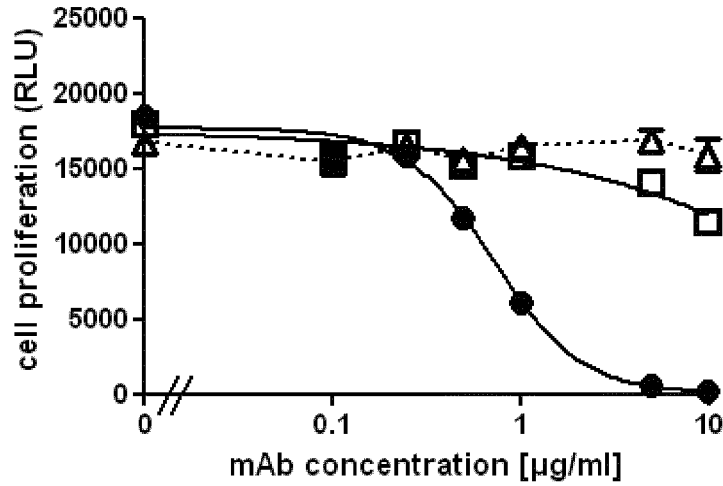

FIGS. 11A and B: Inhibition of prolactin-induced proliferation of BaF3 cells (monoclonal cells stably transfected with the rhesus prolactin receptor) by neutralizing prolactin receptor antibodies and unspecific control antibodies. The $IC_{50}$ values were determined for the following antibodies in IgG1 format: Mat3 (closed circles), $IC_{50}$=4.6 nM [99.1% inhibition at 1 μg/ml (=6.7 nM)] (see FIG. 11A); HE06.642 (open squares), $IC_{50}$=206 nM [92.4% inhibition at 240 μg/ml (=1600 nM)] (see FIGS. 11A and B); unspecific control antibody (open triangles): no inhibitory effect (see FIGS. 11A and B).

Figure 12:
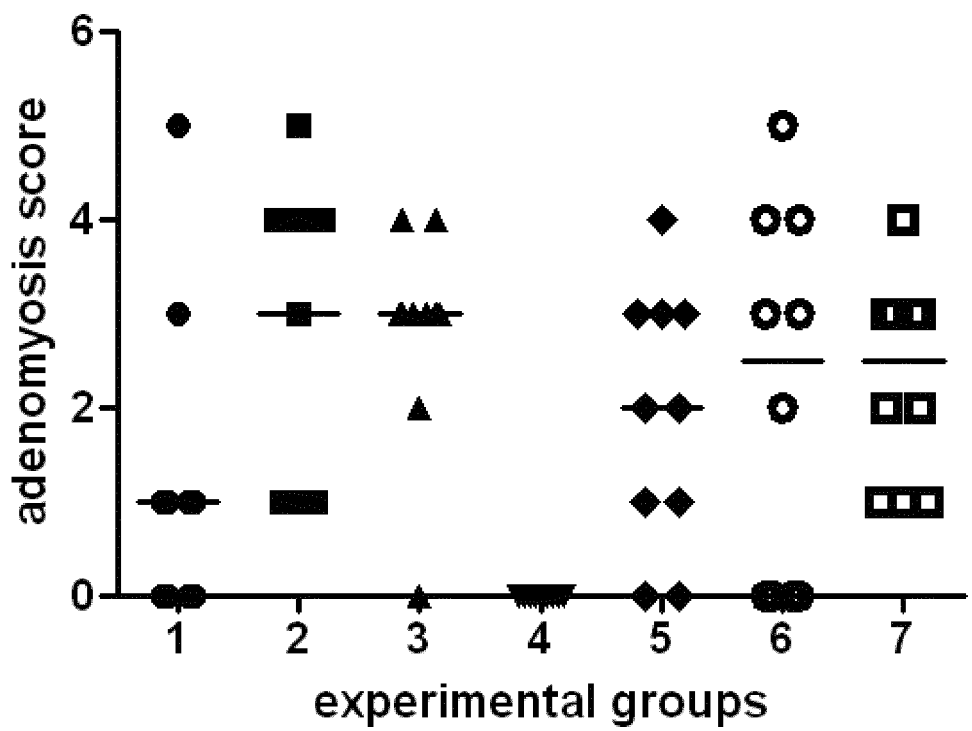

FIG. 12: Treatment of adenomyosis uteri (=endometriosis interna) in SHN mice with neutralizing PRLR antibody Mat3. The results are depicted on the y-axis as disease scores (adenomyosis scores) as described in Example 5. The median disease score for each experimental group is indicated as a horizontal bar. The experimental groups are the following ones: group 1, no pituitary isograft (normoprolactinemic mice develop endometriosis interna to some degree, median disease score=1); group 2, with pituitary isograft (hyperprolactinemia due to pituitary isografting enhances the disease score, median disease score=3); group 3, with pituitary isograft treated with unspecific murine IgG2a isotype control antibody once weekly at a dose of 30 mg/kg (median disease score=3); group 4, with pituitary isograft treated with antibody Mat3 in the murine IgG2a format (Mat3-mIgG2a) once weekly at a dose of 30 mg/kg (Mat3 completely cured the animals. The disease score after 30 mg/kg Mat3 given once weekly was even lower (median disease score=0) than the disease score of normoprolactinemic mice (median disease score=1); group 5, with pituitary isograft treated with antibody Mat3-mIgG2a once weekly at a dose of 10 mg/kg (median disease score=2); group 6, with pituitary isograft treated with antibody Mat3-mIgG2a once weekly at a dose of 3 mg/kg (median disease score=2.5); group 7, with pituitary isograft treated with antibody Mat3-mIgG2a once weekly at a dose of 1 mg/kg (median disease score=2.5). Treatment with antibody Mat3 shows a dose-dependent decrease in the median disease score. Mat3 is therefore suitable to treat endometriosis interna (=adenomyosis uteri) and endometriosis externa in women.

Figure 13A:
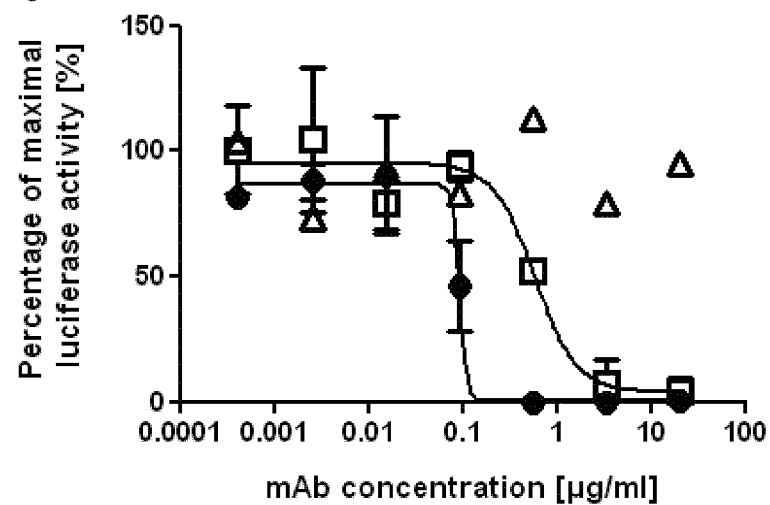
Figure 13B:
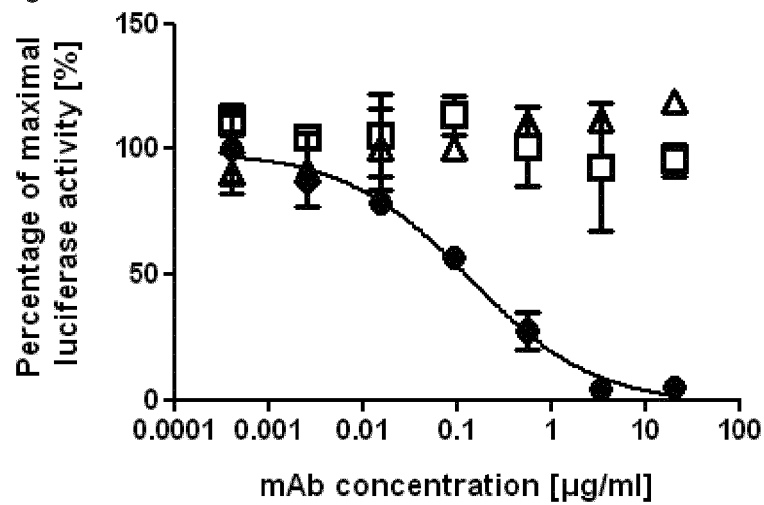

FIGS. 13A and B: Inhibition of luciferase reporter gene activity in HEK293 cells stably transfected with the human and murine PRLR. In FIG. 13A the human PRLR-dependent activity is plotted against the antibody concentrations, while FIG. 13B shows the murine PRLR-dependent activity. The luciferase activity is given as percentage of the maximal luciferase activity obtained without addition of any antibody. The $IC_{50}$ values were determined for the following antibodies in IgG1 format: Mat3 (closed circles), $IC_{50}$=0.5 nM (FIG. 13A, hPRLR) and 1.3 nM (FIG. 13B, mPRLR); HE06.642 (open squares), $IC_{50}$=4.6 nM (FIG. 13A, hPRLR) and >>1333 nM (=20 μg/ml) (FIG. 13B, mPRLR); unspecific isotype control antibody (open triangles): no inhibitory effect (see FIGS. 13A and B). These data show the improved activity of Mat3 on hPRLR compared to HE06.642 and demonstrate the activity of Mat3 on mPRLR whereas HE06.642 does not inhibit mPRLR-dependent luciferase activity.

Figure 14:
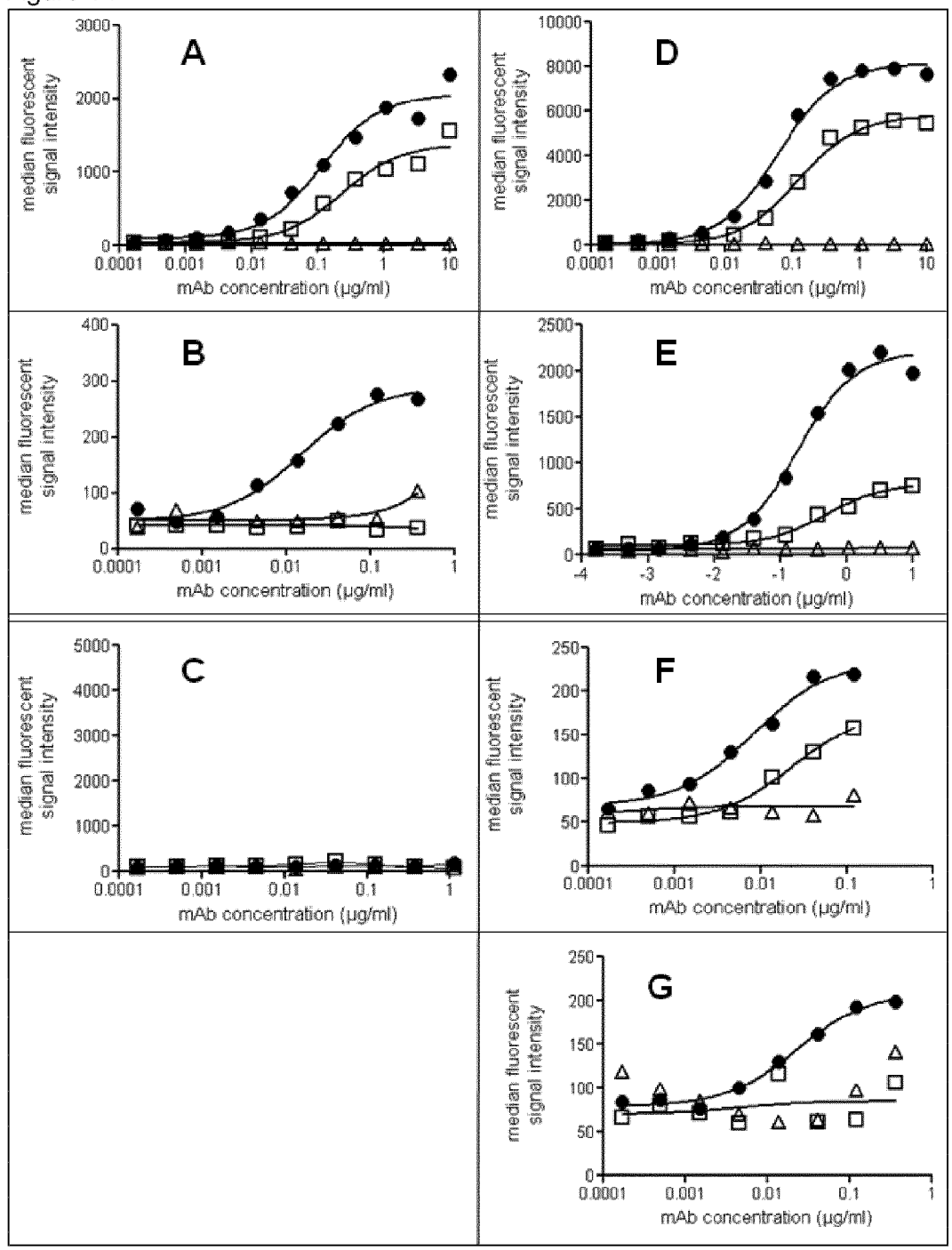

FIG. 14: Cell binding of neutralizing PRLR antibodies on cells expressing PRLR from human, mouse and monkey using flow cytometry. The median fluorescent signal intensity is plotted against the antibody concentration. The following IgG1 antibodies were applied: Mat3 (closed circles), HE06.642 (open squares), unspecific isotype control antibody (open triangles). Different cell lines were tested: A) HEK293 cell line stably transfected with human PRLR, B) HEK293 cell line stably transfected with murine PRLR, C) HEK293 cell line not transfected with any PRLR gene (negative control cell line). D) human breast cancer cell line T47D, E) BaF3 cell line stably transfected with rhesus monkey PRLR, F) BaF3 cell line stably transfected with human PRLR, G) BaF3 cell line stably transfected with murine PRLR. The cell line binding potency of the antibodies on the different cell lines have been deduced from the dose-response curves as $EC_{50}$ values (see Table 8). The dose-response plots indicate the superior cell binding properties of Mat3 compared to HE06.642.

Seq ID NO:1 represents amino acid sequence of VH, Mat3
Seq ID NO:2 represents amino acid sequence of VL, Mat3
Seq ID NO:3 represents nucleic acid sequence VH, Mat3
Seq ID NO:4 represents nucleic acid sequence VL, Mat3
Seq ID NO:5 represents amino acid sequence of HCDR1, Mat3
Seq ID NO:6, represents nucleic acid sequence HCDR2, Mat3
Seq ID NO:7 represents nucleic acid sequence HCDR3, Mat3
Seq ID NO:8 represents nucleic acid sequence LCDR1, Mat3
Seq ID NO:9 represents nucleic acid sequence LCDR2, Mat3
Seq ID NO:10 represents nucleic acid sequence LCDR3, Mat3
Seq ID NO:11 represents amino acid sequence of extracellular domain of cynomolgus and rhesus monkey PRLR fused to Fc-His
Seq ID NO:12 represents human ECD_PRLR, amino acid position 1-210, 51 domain 1-100 (51 domain construct 1-102), S2 domain 101-210
Seq ID NO:13 represents murine ECD_PRLR, amino acid position 1-210
Seq ID NO:14 represents amino acid sequence of VH, HE06642, Novartis (WO2008/22295)
Seq ID NO:15 represents amino acid sequence of VL, HE06642, Novartis (WO2008/22295)
Seq ID NO:16 represents nucleic acid sequence VH, HE06642, Novartis (WO2008/22295)
Seq ID NO:17 represents nucleic acid sequence VL, HE06642, Novartis (WO2008/22295)

EXAMPLES

Example 1

Inhibition of Prolactin-Induced Proliferation of BaF3 Cells (Monoclonal Cells Stably Transfected with Human Prolactin Receptor) by Neutralizing Prolactin Receptor Antibodies and Unspecific Control Antibodies To analyze the in vitro efficacy of the neutralizing PRLR antibodies, the inhibition of prolactin-activated cellular proliferation of BaF3 cells was used. The cells were stably transfected with human PRLR and were routinely cultured in RPMI containing 2 mM glutamine in the presence of 10% FCS and 10 ng/ml of human prolactin. After six hours of starvation in prolactin-free medium containing 1% FCS, cells were seeded into 96-well plates at a density of 25000 cells per well. Cells were stimulated with 35 ng/ml prolactin and coincubated with increasing doses of neutralizing PRLR antibodies for two days. Cellular proliferation was analyzed using a CellTiter-Glo Luminescent Cell Viability Assay (Promega). Dose-response curves for the inhibition of prolactin-stimulated cellular growth were generated and $IC_{50}$ values calculated. As negative control, stimulation with an unspecific control antibody was used. Antibody Mat3 was tested in comparison to antibody HE 06.642 (both were in the IgG1 format) (FIG. 9).

Example 2

Inhibition of Prolactin-Induced Proliferation of BaF3 Cells (Monoclonal Cells Stably Transfected with the Murine Prolactin Receptor) by Neutralizing Prolactin Receptor Antibodies And Unspecific Control Antibodies To analyze the in vitro efficacy of the neutralizing PRLR antibodies, the inhibition of prolactin-activated cellular proliferation of Ba/F3 cells was used. The cells were stably transfected with the murine PRLR and were routinely cultured in RPMI containing 2 mM glutamine in the presence of 10% FCS and 10 ng/ml of human prolactin. After six hours of starvation in prolactin-free medium containing 1% FCS, cells were seeded into 96-well plates at a density of 20000 cells per well. Cells were stimulated with 50 ng/ml prolactin and coincubated with increasing doses of neutralizing PRLR antibodies for three days. Cellular proliferation was analyzed using a CellTiter-Glo Luminescent Cell Viability Assay (Promega). Dose-response curves for the inhibition of prolactin-stimulated cellular growth were generated and $IC_{50}$ values calculated. As negative control, stimulation with an unspecific control antibody was used. Antibody Mat3 was tested in comparison to antibody HE 06.642 (both were in the IgG1 format) (FIG. 10).

Example 3

Figure 11B:
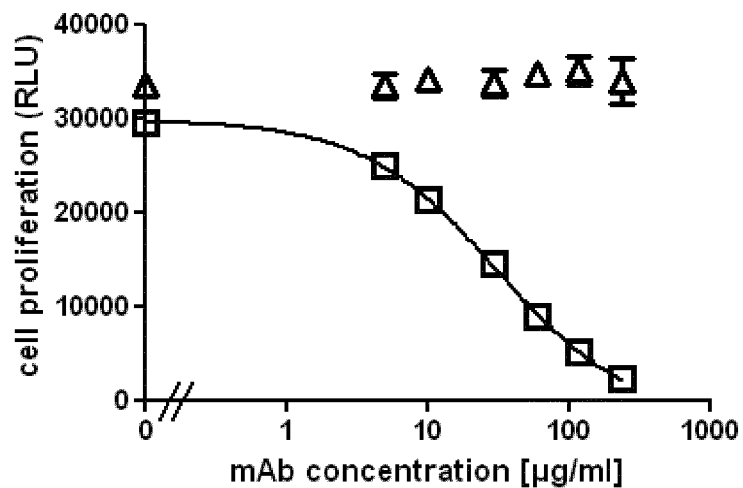

Inhibition of Prolactin-Induced Proliferation of BaF3 Cells (Monoclonal Cells Stably Transfected with the Rhesus Prolactin Receptor) by Neutralizing Prolactin Receptor Antibodies and Unspecific Control Antibodies To analyze the in vitro efficacy of the neutralizing PRLR antibodies, the inhibition of prolactin-activated cellular proliferation of Ba/F3 cells was used. The cells were stably transfected with the rhesus PRLR and were routinely cultured in RPMI containing 2 mM glutamine in the presence of 10% FCS and 10 ng/ml of human prolactin. After six hours of starvation in prolactin-free medium containing 1% FCS, cells were seeded into 96-well plates at a density of 25000 cells per well. Cells were stimulated with 100 ng/ml prolactin and coincubated with increasing doses of neutralizing PRLR antibodies for two days. Cellular proliferation was analyzed using a CellTiter-Glo Luminescent Cell Viability Assay (Promega). Dose-response curves for the inhibition of prolactin-stimulated cellular growth were generated and $IC_{50}$ values calculated. As negative control, stimulation with an unspecific control antibody was used. Antibody Mat3 was tested in comparison to antibody HE 06.642 (both were in the IgG1 format) (FIG. 11).

Example 4

Quantitative Analysis of Prolactin and Prolactin Receptor Gene Expression by Real-Time TaqMan PCR Analysis in eu- and Ectopic Endometrium and Endometriotic Lesions from Patients and Healthy Controls Real-timeTaqman PCR analysis was performed using the ABI Prism 7700 Sequence Detector System according to the manufacturer's instructions (PE Applied Biosystems) and as described Endocrinolgy 2008, 149 (8): 3952-3959) and known by the expert in the field. Relative expression levels of PRL and the PRLR were normalized to the expression of cyclophyllin. We analyzed the expression of PRL and the PRLR in the endometrium from healthy women and in endometrium and endometriotic lesions from patients by using quantitative real-time Taqman PCR analysis. The expression of prolactin and its receptor was clearly upregulated in endometriotic lesions compared to healthy endometrium or endometrium derived from patients.

Results are shown in FIGS. 1 and 2.

These findings imply that autocrine prolactin signalling plays a role in the development and maintenance of endometriosis and adenomyosis uteri (endometriosis interna, a form of endometriosis restricted to the uterus.

Example 5

Treatment of Adenomyosis Uteri (=Endometriosis Interna) in SHN Mice with Neutralizing PRLR Antibody Mat3

To test the efficacy of neutralizing PRLR antibodies in endometriosis, the adenomyosis uteri model in SHN mice relying on systemic hyperprolactinemia was employed (Acta anat. 116:46-54, 1983). Hyperprolactinemia in SHN mice was induced by pituitary isografting under the kidney capsule of 7 weeks old female mice (Acta anat. 116:46-54, 1983). Neutralizing PRLR antibody Mat3 (30 mg/kg; 10 mg/kg, 3 mg/kg, 1 mg/kg) or unspecific antibody (30 mg/kg) were administered subcutaneously starting two weeks after pituitary isografting. Animals were treated once weekly with the antibodies for seven weeks. The infiltration of the uterine muscular layer by glandular tissue was assessed as described previously (Laboratory Animal Science 1998, 48:64-68). At autopsy (day 66 after pituitary transplantation), uteri were fixed overnight in buffered 4% formalin and embedded in paraffin. The degree of adenomyosis (=endometriosis interna) was assessed as follows:

Grade 0=no adenomyosis
Grade 1=the inner layer of the myometrium looses its concentric orientation
Grade 2=endometrial glands invading the inner layer of the myometrium
Grade 3=endometrial glands between the inner and outer layer of the uterine myometrium
Grade 4=endometrial glands invading the outer layer of the uterine myometrium
Grade 5=endometrial glands outside of the outer layer of the uterine myometrium The experiment comprised the following experimental groups:

1. Animals without pituitary transplantation, i.e. nommoprolactinemic mice
2. Animals with pituitary transplantation, i.e. hyperprolactinemic mice
3. Animals with pituitary transplantation, treated with unspecific control antibody once weekly at a dose of 30 mg/kg
4. Animals with pituitary transplantation, treated with the neutralizing prolactin receptor antibody Mat3 in the murine IgG2a format once weekly at a dose of 30 mg/kg
5. Animals with pituitary transplantation, treated with the neutralizing prolactin receptor antibody Mat3 in the murine IgG2a format once weekly at a dose of 10 mg/kg 6. Animals with pituitary transplantation, treated with the neutralizing prolactin receptor antibody Mat3 in the murine IgG2a format once weekly at a dose of 3 mg/kg
7. Animals with pituitary transplantation, treated with the neutralizing prolactin receptor antibody Mat3 in the murine IgG2a format once weekly at a dose of 1 mg/kg The neutralizing PRLR antibody Mat3 inhibited endometriosis interna (=adenomyosis) (FIG. 12). The neutralising PRLR antibody Mat3 is therefore suitable to treat endometriosis interna (=adenomyosis uteri) and endometriosis externa in women.

Example 6

Neutralizing PRLR Antibody Mat3 is Suitable for the Treatment of Benign Breast Disease An activating PRLR mutation or local or systemic hyperprolactinemia can provoke benign breast disease. Therefore, a hyperprolactinemic mouse model with enhanced proliferation in the mammary gland (hallmark of the most severe forms of benign breast disease) was employed. 12 weeks old female Balb/c mice received a pituitary isograft under the kidney capsule or remained unoperated. Pituitary isografted mice remained untreated or were treated subcutaneously once weekly with neutralizing PRLR antibody Mat3 in the IgG2 format (=IgG2 Mat3) or unspecific control antibody in IgG2 format on day 15, 22, 29, and 36 after pituitary transplantation. Antibody doses were 30 mg/kg. Experimental group size was 8 animals.

The experiment comprised the following experimental groups:
1. Animals without pituitary transplantation, i.e. nommoprolactinemic mice
2. Animals with pituitary transplantation, i.e. hyperprolactinemic mice
3. Animals with pituitary transplantation, treated with unspecific control antibody once weekly at a dose of 30 mg/kg
4. Animals with pituitary transplantation, treated with the neutralizing prolactin receptor antibody Mat3 once weekly at a dose of 30 mg/kg On day 38 after pituitary transplantation mice were sacrificed. Two hours before death, animals received an intraperitoneal injection of BrdU to monitor epithelial cell proliferation. The left inguinal mammary gland was fixed in Carnoy's solution and mammary gland whole mounts were prepared and stained with Carmine alaune. Side-branching was evaluated in the mammary gland whole mounts. Results are depicted in FIG. 3A. Antibody Mat3 inhibited sidebranching in the mammary gland, unspecific control antibody was without effect (FIG. 3A).

Afterwards the mammary gland whole mounts were embedded in paraffin and BrdU immunostainings were performed as described previously (Endocrinology 149 (8): 3952-3959; 2009). Epithelial cell proliferation was analysed in 4 histological mammary gland slices per animal.

The lateral one third of the right inguinal mammary gland without the lymph node was frozen in liquid nitrogen and processed for RNA preparation. After reverse transcription, real-time Taqman PCR analysis was performed using the ABI Prism 7700 Sequence Detector System according to the manufacturer's instructions (PE Applied Biosystems). Expression of the prolactin target gene elf5 was assessed and normalized to cytokeratin18 expression. Relative mRNA levels were calculated by the comparative ΔCT-method. Pituitary isografting, i.e. hyperprolactinemia enhanced expression of the prolactin target gene elf5 (FIG. 3B). Specific antibody Mat3, but not the unspecific control antibody inhibited elf5 gene expression indicating successful blockade of the prolactin receptor (FIG. 3B).

Antibody Mat3 is therefore suitable to treat benign breast disease.

Example 7

Isolation of Target-Specific Antibodies from Human Antibody Phage Display Libraries To isolate a panel of antibodies able to neutralize the activity of human PRLR, three human antibody phage display libraries, expressing Fab and scFv fragments, were investigated in parallel. The target used for the library panning was the soluble extracellular domain (ECD) of the human and mouse prolactin receptor, respectively, represented by the amino acids 1-210, of SEQ ID NOs. 12 and 13. Alternative targets were the ECD of PRLR C-terminally linked to six histidines or to a human IgG1-Fc domain via the linker with the amino acid sequence "isoleucine-glutamate-glycine-arginine-methionine-aspartate".

Selection of target-specific antibodies from phage display was carried out according to methods described by Marks et al. (Methods Mol. Biol. 248:161-76, 2004). The phage display library was incubated with 50 pmols of the biotinylated ECD at room temperature for 1 hr and the complex formed was then captured using 100 µl of Streptavidin beads suspension (Dynabeads® M-280 Streptavidin, Invitrogen). Non specific phages were removed by washing the beads with wash buffer (PBS+5% Milk). Bound phages were eluted with 0.5 ml of 100 nM Triethylamine (TEA,) and immediately neutralized by addition of an equal volume of IM TRIS-CI pH 7.4. Eluted phage pool was used to infect TG1 *E. coli* cells growing in logarithmic phase, and phagemid was rescued as described (Methods Mol. Biol. 248:161-76, 2004). Selection was repeated for a total of three rounds. Single colonies obtained from TG1 cells infected with eluted phage from the third round of panning were screened for binding activity in an ELISA assay. Briefly, single colonies obtained from the TG1 cell infected with eluted phage were used to inoculate media in 96-well plates.

Microcultures were grown to an $OD_{600}$=0.6 at which point expression of soluble antibody fragment was induced by addition of 1 mM IPTG following overnight culture in a shaker incubator at 30° C. Bacteria were spun down and periplasmic extract was prepared and used to detect antibody binding activity to ECD immobilized on 96-well microplates (96-well flat bottom Immunosorb plates. Nunn) following standard ELISA protocol provided by the microplate manufacturer.

The affinities of the anti-Prolactin Receptor (PRLR) antibodies for binding to the recombinant extracellular domain (ECD) were estimated using the Biacore® 2000 and used for affinity ranking of antibodies.

Example 8

Maturation of Antibody Variants

Antibody affinity maturation is a two step process where saturation mutagenesis and well-based high throughput screening are combined to identify a small number of mutations resulting in affinity increases. In the first round of affinity maturation positional diversification of wild-type antibody is introduced by site-directed mutagenesis using NNK-trinucleotide cassettes (whereby N represents a 25% mix each of adenine, thymine, guanine, and cytosine nucleotides and K represents a 50% mix each of thymine and guanine nucleotides) according to BMC Biotechnology 7: 65, 2007. This way, all 20 amino acids are introduced at an individual amino acid position. This positional randomization is restricted to the six complementarity determining regions (CDRs). In the second round of affinity maturation beneficial substitutions were recombined and screened for further improvements.

Screening of Maturated "005-C04" Fab Variants by ELISA Tests:

96 well microtiter plates were coated with 1 µg per milliliter of human PRLR. Plates were incubated over night at 4° C. After blocking with PBS buffer containing 3% bovine serum albumin, normalized E. coli-derived supernatants containing the Fab variants were added. Detection of formed complexes occurred via the addition of an anti-flag antibody (Sigma, A8592) labeled with horseradish peroxidase.

Figure 7:
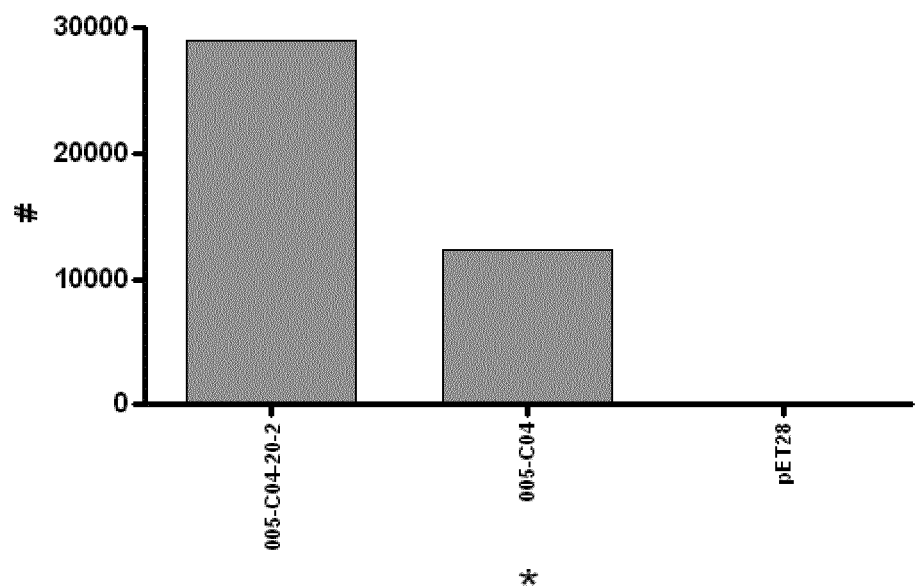
FIG. 7: ELISA-based binding tests of a maturated Fab variant.

Amplex Red as fluorogenic substrate for horseradish peroxidase was added and incubated for 30 minutes at room temperature. Absorption at 570 nm and extinction at 585 nm was measured using the Tecan Infinite F500 reader. The obtained results the screening hit "005-004-20-2" are shown in FIG. 7. Individual substitutions in the screening hit "005-004-20-2" (FIG. 7) beneficial for affinity improvement were evaluated regarding their influence on thermostability of the Fab antibody, in order to ensure cooperative unfolding of the Fab domain during denaturation by temperature elevation. The antibody Mat3 was a derivative of "005-004-20-2", in which the thermo-destabilizing substitutions have been reversed to the parental antibody "005-004".

Example 9

Cross-Reactivity of Antibodies on Mouse and Human PRLR Expressed on Cell Surfaces a) In order to understand the missing antiproliferative activity of antibody HE06642 on cells carrying the murine PRLR, the binding characteristics of HE06642 on mouse and human PRLR expressed on cells was determined by flow cytometry on HEK293 cells stably expressing the human and murine PRLR, respectively. The cells as well as the parental HEK293 cell line without PRLR were harvested, centrifuged and resuspended at approximately $5\times10^6$ cells/ml in 1×PBS containing 2% FBS and 0.1% sodium azide (FACS buffer). The antibody HE06642 was diluted to 2-fold final concentration in FACS buffer and added to appropriate sample wells (50 µl/well). For secondary antibody and autofluorescence controls, 50 µl FRCS buffer was added to appropriate wells. 50 µl of cell suspension was added to each sample well. Samples were incubated at 4° C. for one hour, washed twice with cold FACS buffer and resuspended in FACS buffer containing PE-conjugated goat anti-human IgG at a 1:100 dilution. Following a 30 min incubation at 4° C., cells were washed twice with cold FACS buffer, resuspended in FACS buffer containing 1 mg/ml propidium iodide (Invitrogen, San Diego, Calif.) and analyzed by flow cytometry. As shown in FIG. 5A, the antibody HE06.642 only binds to the human PRLR and not to the murine PRLR. This observation is consistent with the finding reported in Example 2 and 12 about the missing activity of HE06.642 in the murine PRLR-dependent proliferation and luciferase reporter gene assays.

b) In order to demonstrate cell binding of antibody Mat3 on cells carrying the human and the rhesus monkey PRLR, of which the amino acid sequence of the extracellular domain is identical to the one of cynomolgus monkey, the binding characteristics of Mat3 on human and monkey PRLR expressed on cells was determined by flow cytometry on HEK293 cells stably expressing the human and monkey PRLR, respectively. The cells were harvested, centrifuged and resuspended at approximately $2\times10^6$ cells/ml in 1×PBS containing 3% FBS and 0.05% sodium azide (FACS buffer). The antibody Mat3 was diluted to 2-fold final concentration in FACS buffer and added to appropriate sample wells (50 µl/well). For secondary antibody and autofluorescence controls, 50 µl FACS buffer was added to appropriate wells. 50 µl of cell suspension was added to each sample well. Samples were incubated at 4° C. for one hour, washed twice with cold FRCS buffer and resuspended in FACS buffer containing PE-conjugated goat anti-human IgG at a 1:100 dilution. Following a 30 min incubation at 4° C., cells were washed twice with cold FACS buffer, resuspended in FACS buffer containing 1 mg/ml propidium iodide (Invitrogen, San Diego, Calif.) and analyzed by flow cytometry. As shown in FIG. 5B, the antibody Mat3 binds to the human PRLR as well as to the monkey PRLR. Maximal signal intensities at highest antibody concentrations depend on the number of PRLR expressed on the cell surfaces, i.e. HEK293 and Ba/F cells do not carry the same number of PRLRs on their surface. The EC50 values were calculated based on the dose response curves illustrated in FIG. 5B, in order to derive a measurement value for binding strength of Mat3 on cells (Table 2). The cell-based binding potency of Mat3 was 0.53 nM on HEK293 cells with human PRLR and 2.94 nM on Ba/F cells with monkey PRLR. These data support the finding that Mat3 is not only a very potent human-specific agent, but also at reasonable doses active on monkey PRLR in the low nanomolar range.

Example 10

Binding Studies with Purified Extracellular PRLR Domains Using Surface Plasmon Resonance Analysis Binding affinities of antibody Mat3 were determined by surface plasmon resonance analysis on a Biacore T100 instrument (GE Healthcare Biacore, Inc.). Antibodies were immobilized onto a CM5 sensor chip through an indirect capturing reagent, anti-human IgG Fc. Reagents from the "Human Antibody Capture Kit" (BR-1008-39, GE Healthcare Biacore, Inc.) were used as described by the manufacturer. Approximately 5000 RU monoclonal mouse anti-human IgG (Fc) antibody were immobilized per cell. Antibody Mat3 was injected at a concentration of 5 µg/ml at 10 µl/min for 10 sec to reach a capturing level of approximately 200 to 600 RU. Various concentrations (400 nM, 200 nM, 100 nM, 50 nM, 25 nM, 12.5 nM, 6.25 nM, and 3.12 nM) in HEPES-EP buffer (GE Healthcare Biacore, Inc.) of the ECD of human, monkey or murine PRLR were injected over immobilized Mat3 antibody at a flow rate of 60 µl/min for 3 minutes and the dissociation was allowed for 10 minutes. The ECDs of the human PRLR (SEQ ID NO: 12), of the monkey PRLR (SEQ ID NO: 11, after proteolytic removal of the Fc-His-tag via Factor Xa digestion) and of the murine PRLR (SEQ ID NO: 13) represented monovalent analytes. Sensograms were generated after in-line reference cell correction followed by buffer sample subtraction. The dissociation equilibrium constant ($K_D$) was calculated based on the ratio of association (kon) and dissociation rated (koff=kd) constants, obtained by fitting sensograms with a first order 1:1 binding model using BiaEvaluation Software. The monovalent dissociation constants ($K_D$, affinity) and dissociation rates (kd=koff) values are shown in Table 1.

Example 11

Peptide Scan a) Peptide Synthesis:

To reconstruct discontinuous epitopes of the target molecule SEQ ID NO. 12 from amino acid position 1 to 210, the ECD of the human PRLR, a library of structured peptides was synthesized. This was done using Pepscan's proprietary Chemically Linked Peptides on Scaffolds (CLIPS) technology (Timmerman at al., 2007, J. Mol. Recognit. 20:283-99; Pepscan Therapeutics, Lelystad, Netherlands). CLIPS technology allows to structure peptides into single loops, double-loops, triple loops, sheet-like folds, helix-like folds and combinations thereof. CLIPS templates were coupled to cysteine residues. The side-chains of multiple cysteines in the peptides were coupled to one or two CLIPS templates. For example, a 0.5 mM solution of the T2 CLIPS template 1,3-bis (bromomethyl) benzene was dissolved in ammonium bicarbonate (20 mM, pH 7.9)/acetonitrile (1:1(v/v). This solution was added onto the peptide arrays. The CLIPS template bound to side-chains of two cysteines as present in the solid-phase bound peptides of the peptide-arrays (455 wells plate with 3 ul wells). The peptide arrays were gently shaken in the solution for 30 to 60 minutes while completely covered in solution. Finally, the peptide arrays were washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

b) Pepscan ELISA:

The binding of antibody Mat3 and of antibody HE06642 to each peptide was tested in a PEPSCAN-based ELISA (Slootstra at al., 1996, Molecular Diversity 1: 87-96). The peptide arrays were pre-incubated with 5% to 100%-binding buffer (1 hr, 20° C.). The binding buffer was composed of 1% Tween-80, 4% horse-serum, 5% Ovalbumin (w/v) and was diluted with PBS. After washing the peptide arrays were incubated with primary antibody solution (1 to 5 µg/ml) in PBS containing 1% Tween-80 (overnight at 4° C.). After washing, the peptide arrays were incubated with a 1/1000 dilution in 100% binding buffer of an antibody peroxidase conjugate for one hour at 25° C. (anti-human, humpo). After washing, the peroxidase substrate 2,2'-azino-di-3-ethylbenzthiazoline sulfonate (ABTS) and 2 microliters/milliliter of 3 percent $H_2O_2$ were added. After one hour, the color development was measured. The color development was quantified with a charge coupled device (CCD)—camera and an image processing system.

c) Data Processing:

The raw data were optical values obtained by a CCD-camera. The values ranged from 0 to 3000 mAU, similar to a standard 96-well plate ELISA-reader. The results were quantified and stored into the Peplab database. The binding values were extracted for analysis. Occasionally a well contained an air-bubble resulting in a false-positive value, the cards were manually inspected and any values caused by an air-bubble were scored as 0.

d) Data Analysis and Representation:

A heat map is a graphical representation of data where the empirical values from experimental data are organized in a two-dimensional map, and are then represented as colors (Brinton, 1914, Graphic Methods for Presenting Facts, New York: The Engineering Magazine Company; Gower and Digby, 1981), "Expressing complex relationships in two dimensions" in Interpreting Multivariate Data, ed. Barnett. V., Chichester, UK: John Wiley & Sons, pp. 83-118). For double-looped CLIPS peptides, such a two-dimensional map could be derived from the independent sequences of the first loop and the second loop.

For the target protein (ECD of human PRLR), the 2916 CLIPS peptides had sequences that were effectively permutations of 54 unique sub-sequences, combined in two sequential CLIPS loops. Thus, the observed Pepscan ELISA data could be plotted in a 54×54 matrix, where each X coordinate was the amino acid sequence of the first loop, and each Y coordinate was the amino acid sequence of the second loop. For each XY coordinate in the matrix, the Pepscan ELISA value was placed that is derived from the peptide with sequence X+Y. To further facilitate the visualization, Pepscan ELISA values were replaced with colors from a continuous gradient. In this case, extremely low values were colored green, extremely high values were colored red, and average values were colored black. When this color map was applied to the described data matrix, a color heat map resulted. The peptides revealing the most striking differences in the ELISA results between the antibodies Mat3 and HE06642 were selected based on these heat map representation. For these peptides, each ELISA signal value was processed for representation in a bar plot (FIGS. 8A and 8B). Each plotted value represented the average value obtained for 54 peptides with S.E.M (standard error of mean). The data was normalized to average over the entire 2916 peptide dataset and corrected for background signal.

FIG. 8A shows the ELISA results for a subset of peptides ranging from amino acids 103-PDPPLELAVEVKQPE-117 indicated as '117' on the X-axis to 127-WSPPTLIDLKTG-WFT-141 (indicated as '141'). I. e. these peptides, which were shifted by three amino acids along the ECD amino acid sequence, cover the region from amino acid position 103 to 141 of the ECD of human PRLR. The strongest differences observed within this dataset are for peptide 109-LAVEVKQPEDRKPYL-123 (indicated as '123') with a significance p-value of $4 \times 10^{-12}$, and for peptide 121-PYLWIK-WSPPTLIDL-135 (indicated as '135') with a significance p-value of $7 \times 10^{-40}$.

FIG. 8B shows the ELISA results for a subset of peptides ranging from 139-WFTLLYEIRLKPEKA-153 (indicated as '153' on the X-axis) to 163-QQTEFKILSLHPGQK-177 (indicated as '177'). I. e. these peptides, which were shifted by three amino acids along the ECD amino acid sequence, cover the region from amino acid position 139 to 177 of the ECD of human PRLR. The strongest differences observed within this dataset are for peptide 148-LKPEKAAEWEIHFAG-162 (indicated as '162') with a significance p-value of $6 \times 10^{-26}$, and for peptide 160-FAGQQTEFKILSLHP-174 (indicated as '174') with a significance p-value of $8 \times 10^{-8}$.

These data demonstrate that both antibodies bind to the S2 subdomain of the ECD of human PRLR (amino acid 101 to 210) and therefore are non-competitive to the natural ligand PRL which mainly binds to the S1 domain. However, this peptide scan showed that there are differences in binding to the S2 domains between Mat3 and HE06642. This finding indicates why the antibody Mat3 shows a different species-specificity and potency compared to HE06642.

Example 12

Inhibition of Luciferase Reporter Gene Activity in HEK293 Cells Stably Transfected with the Human and Murine PRLR To further analyze the in vitro activity of the neutralizing PRLR antibody Mat3 on the human and the murine PRLR, a reporter gene assay was used. HEK293 cells stably transfected with the murine PRLR were transiently transfected with a luciferase reporter gene under the control of LHREs (lactogenic hormone response elements). Afterwards, cells were seeded at a density of 20000 cells per well (80 µl) on a 96-well plate in DMEM High Glucose medium with 4.5 g/L glucose, 2 mM Glutamax, 0.5% FCS, and 1% Penicillin/Streptomycin. The next day 200 ng/ml human prolactin (10 µl) with and without increasing doses of test antibodies (10 µl) were added. Twenty-four hours later, luciferase activity was determined. For comparison, the antibody HE06642 and a non-specific antibody targeting choleratoxin called CTX were also tested. All antibodies were tested as IgG1 molecules (FIGS. 13A and 13B).

Example 13

Binding Studies with Purified Extracellular PRLR Domains Using Surface Plasmon Resonance Analysis Binding affinities of antibodies Mat3 and HE06642 were determined by surface plasmon resonance analysis on a Biacore T100 instrument (GE Healthcare Biacore, Inc.) in parallel. Antibodies were immobilized onto a CM5 sensor chip through an indirect capturing reagent, anti-human IgG Fc. Reagents from the "Human Antibody Capture Kit" (BR-1008-39, GE Healthcare Biacore, Inc.) were used as described by the manufacturer. Approximately 5000 RU monoclonal mouse anti-human IgG (Fc) antibody were immobilized per cell. Each test antibody was injected at a concentration of 5 µg/ml at 10 µl/min for 10 sec to reach a capturing level of approximately 200 to 600 RU. Various concentrations (400 nM, 200 nM, 100 nM, 50 nM, 25 nM, 12.5 nM, 6.25 nM, and 3.12 nM) in HEPES-EP buffer (GE Healthcare Biacore, Inc.) of the ECD of human, monkey or murine PRLR were injected over the immobilized test antibody at a flow rate of 60 µl/min for 3 minutes and the dissociation was allowed for 10 minutes. The ECDs of the human PRLR (SEQ ID NO: 12), of the monkey PRLR (SEQ ID NO: 11, after proteolytic removal of the Fc-His-tag via Factor Xa digestion) and of the murine PRLR (SEQ ID NO: 13) represented monovalent analytes. Sensograms were generated after in-line reference cell correction followed by buffer sample subtraction. The dissociation equilibrium constant (KD) was calculated based on the ratio of association (kon) and dissociation rated (koff=kd) constants, obtained by fitting sensograms with a first order 1:1 binding model using BiaEvaluation Software (see Table 7).

hPRLR compared to HE06.642. Despite binding to the purified ECD of murine PRLR. HE06.642 does not bind cells or inhibits proliferation of cells expressing the murine PRLR (FIGS. 10 and 14. Table 8). In contrast, Mat3 blocks cell proliferation in nanomolar to subnanomolar scale in all three species.

Additionally, the soluble ECD-PRLR (SEQ ID NO: 12) was captured on the surface via the immobilized test antibodies Mat3 and HE06642, therefore, the epitope of the capture antibody was blocked for all bound ECD-PRLR molecules. Human PRL was immediately passed over the surface to bind to the immobilized ECD-PRLR. This way, it could be measured whether PRL bound the ECD-PRLR, although the ECD is captured by the test antibody.

It could be observed that PRL binds the ECD-PRLR independently from binding to Mat3 and HE06.642. Thus, both antibodies do not compete with the natural ligand PRL on ECD-PRLR.

Example 14

Cell-Binding Studies of Antibodies on Various Cell Lines Expressing Human, Mouse and Monkey PRLR A cell binding study was performed with antibody Mat3 and HE06642 as well as a choleratoxin-specific isotype control, all being in IgG1 format. The tested cell lines were HEK293 cells stably expressing human and mouse PRLR, respectively, the human breast cancer cell line T47D as well as the Ba/F cell lines expressing human, mouse and rhesus monkey PRLR. The cell binding was determined by flow cytometry on the above mentioned cells. The cells were harvested, centrifuged and resuspended at approximately $2\times10^6$ cella/ml in 1xPBS containing 3% FBS and 0.05% sodium azide (FACS buffer). Each test antibody was diluted to 2-fold final concentration in FACS buffer and added to appropriate sample wells (50 µl/well). For secondary antibody and autofluorescence controls, 50 µl FACS buffer was added to appropriate wells. 50 µl of cell suspension was added to each sample well. Samples were incubated at 4° C. for one hour, washed twice with cold FACS buffer and resuspended in FACS buffer containing PE-conjugated goat anti-human IgG at a 1:100 dilution. Following a 30 min incubation at 4° C., cells were washed twice with cold FACS buffer, resuspended in FACS buffer containing 1 mg/ml propidium iodide (Invitrogen, San Diego, Calif.) and analyzed by flow cytometry.

The obtained data are shown as dose-response curves in FIG. 14. From these curves EC50 values were deduced indi-

TABLE 7

Monovalent dissociation constants and dissociation rates of purified extracellular domains of human, monkey and murine PRLR (expressed in HEK293 cells) determined for Mat3 and HE06.642 by surface plasmon resonance

|  | Human PRLR | | Monkey PRLR | | Murine PRLR | |
| --- | --- | --- | --- | --- | --- | --- |
|  | $K_D$ [M] | Kd [1/s] | $K_D$ [M] | Kd [1/s] | $K_D$ [M] | Kd [1/s] |
| Mat3 | $1.3 \times 10^{-9}$ | $4.14 \times 10^{-4}$ | $9.6 \times 10^{-9}$ | $1.02 \times 10^{-3}$ | $0.4 \times 10^{-9}$ | $1.64 \times 10^{-4}$ |
| HE06.642# | $0.8 \times 10^{-9}$ | $5.33 \times 10^{-4}$ | $17 \times 10^{-9}$ | $5.79 \times 10^{-3}$ | $15.0 \times 10^{-9}$ | $9.10 \times 10^{-3}$ |

The affinities disclosed for HE06642 in WO2008/022295 are $K_D$ (human PRLR) = $2.6 \times 10^{-9}$ M, $K_D$ (monkey PRLR) = $38.9 \times 10^{-9}$ M, and $K_D$ (murine PRLR) = $2.7 \times 10^{-9}$ M.

As shown in Table 7, Mat3 exhibits improved affinities to monkey and murine PRLR compared to HE06.642. The improved cell binding and antiproliferative activity of Mat3 on human PRLR is not reflected by improved affinity to cating the cell binding potencies (Table 8). In conclusion, the data indicate the superior cell binding properties of Mat3 compared to HE06.642 across the different PRLR-expressing cell lines.

TABLE 8

Cell binding potency of neutralizing PRLR antibodies Mat3 and He06.642 in IgG1 format on cells expressing PRLR from human, mouse and monkey deduced from flow cytometry

| # | Cell line | Cell binding ($EC_{50}$ [M]) Mat3 | Cell binding ($EC_{50}$ [M]) HE06.642 |
|---|---|---|---|
| A | HEK293-human PRLR | $0.8 \times 10^{-9}$ | $1.6 \times 10^{-9}$ |
| B | HEK293-murine PRLR | $0.1 \times 10^{-9}$ | —* |
| C | HEK293 w/o PRLR | —* | —* |
| D | Human T47D | $0.4 \times 10^{-9}$ | $0.8 \times 10^{-9}$ |
| E | BaF3-rhesus PRLR | $1.2 \times 10^{-9}$ | $3.2 \times 10^{-9}$ |
| F | BaF3-human PRLR | $0.1 \times 10^{-9}$ | $0.2 \times 10^{-9}$ |
| G | BaF3-mouse PRLR | $0.2 \times 10^{-9}$ | —* |

*no significant binding;
dose-response diagrams in FIG. 14

The invention claimed is:

1. Antibody Mat3 or an antigen-binding fragment thereof which antagonizes prolactin receptor (PRLR)-mediated signaling, wherein the variable heavy chain comprises the sequences of CDR1, CDR2, and CDR3 corresponding to SEQ ID NOS: 5, 6, and 7, respectively, and the variable light chain comprises the sequences of CDR1, CDR2, and CDR3 corresponding to SEQ ID NOS: 8, 9, and 10, respectively, and wherein the antibody or antigen-binding fragment thereof comprises an antigen-binding region that binds specifically to one or more regions of the extracellular domain of human PRLR, said human PRLR is depicted by the amino acid sequence from position 1 to 210 of SEQ ID NO: 12.

2. Antibody Mat3 or antigen-binding fragments thereof according to claim 1, whereby the antibody or antigen-binding fragment thereof comprises a variable heavy region with an amino acid sequence according to SEQ ID NO: 1, and a variable light region with an amino acid sequence according to SEQ ID NO: 2.

3. Antibody or antigen-binding fragment thereof according to claim 1, whereby the affinity to the extracellular domain of human PRLR is less than or equal to about 100 nM.

4. Antibody or antigen-binding fragment thereof according to claim 1, whereby the antibody or antigen-binding fragment thereof consists of an antigen-binding region that binds specifically to one or more regions of the extracellular domain of human PRLR and whereby the affinity is less than or equal to about 10 nM.

5. Antibody or antigen-binding fragment thereof of claim 1 wherein the heavy chain constant domains are modified or unmodified IgG1, IgG2, IgG3 or IgG4.

6. An antibody or antigen-binding fragment of claim 1 that is purified to at least 95% homogeneity by weight.

7. A pharmaceutical composition comprising the antibody or antigen-binding fragment according to claim 1 and a pharmaceutically acceptable carrier comprising excipients and auxiliaries.

8. A kit comprising an antibody or an antigen-binding fragment thereof of claim 1.

9. A method of treatment of endometriosis, benign breast disease, or antiestrogen-resistant breast cancer comprising the step of administering an antibody or antigen-binding fragment thereof according to claim 1.

10. Antibody or antigen-binding fragment thereof according to claim 1, whereby the affinity to the extracellular domain of human PRLR is less than about 30 nM.

11. Antibody or antigen-binding fragment thereof according to claim 1, whereby the affinity to the extracellular domain of human PRLR is less than about 10 nM.

12. Antibody or antigen-binding fragment thereof according to claim 1, whereby the antibody or antigen-binding fragment thereof consists of an antigen-binding region that binds specifically to one or more regions of the extracellular domain of human PRLR and whereby the affinity is less than about 1 nM.

13. Antibody Mat3 or an antigen-binding fragment thereof which antagonizes prolactin receptor (PRLR)-mediated signaling, wherein the variable heavy chain comprises the sequences of CDR1, CDR2, and CDR3 corresponding to SEQ ID NOS: 5, 6, and 7, respectively, and the variable light chain comprises the sequences of CDR1, CDR2, and CDR3 corresponding to SEQ ID NOS: 8, 9, and 10, respectively, and wherein the antibody or antigen-binding fragment thereof comprises an antigen-binding region that binds specifically to one or more regions of the extracellular domain of monkey PRLR, said monkey PRLR is depicted by the amino acid sequence from position 1 to 210 of SEQ ID NO: 11.

14. Antibody Mat3 or an antigen-binding fragment thereof which antagonizes prolactin receptor (PRLR)-mediated signaling, wherein the variable heavy chain comprises the sequences of CDR1, CDR2, and CDR3 corresponding to SEQ ID NOS: 5, 6, and 7, respectively, and the variable light chain comprises the sequences of CDR1, CDR2, and CDR3 corresponding to SEQ ID NOS: 8, 9, and 10, respectively, and wherein the antibody or antigen-binding fragment thereof comprises an antigen-binding region that binds specifically to one or more regions of the extracellular domain of mouse PRLR, said mouse PRLR is depicted by the amino acid sequence from position 1 to 210 of SEQ ID NO: 13.

* * * * *

SEQUENCE LISTING

```
<160> NUMBER OF SEQ ID NOS: 17

<210> SEQ ID NO 1
<211> LENGTH: 118
<212> TYPE: PRT
<213> ORGANISM: Artificial Sequence
<220> FEATURE:
<223> OTHER INFORMATION: 005-C04-mat3-VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Glu Trp Val
            35                  40                  45

Ser Asp Ile Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Ser Ser
        115

<210> SEQ ID NO 2
<211> LENGTH: 113
<212> TYPE: PRT
<213> ORGANISM: Artificial Sequence
<220> FEATURE:
<223> OTHER INFORMATION: 005-C04-mat3-VL

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
                20                  25                  30

Tyr Val Val His Trp Tyr Gln Gln Leu Pro Gly Thr Ala Pro Lys Leu
            35                  40                  45

Leu Ile Tyr Arg Asn Asn Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80
```

```
Arg Ser Glu Asp Glu Ala Asp Tyr Tyr Cys Ala Ala Trp Asp Asp Ser
                85                  90                  95

Leu Asn Gly Trp Leu Phe Gly Gly Gly Thr Lys Leu Thr Val Leu Gly
            100                 105                 110

Gln

<210> SEQ ID NO 3
<211> LENGTH: 354
<212> TYPE: DNA
<213> ORGANISM: Artificial Sequence
<220> FEATURE:
<223> OTHER INFORMATION: 005-C04-mat3-VH

<400> SEQUENCE: 3
gaggtgcagc tgctggaatc cggcggaggc ctggtgcagc ctggcggatc tctgagactg      60
tcctgcgccg cctccggctt caccttctcc agctactgga tgcactgggt ccgacaggcc     120
cctggcaagg gcctggaatg ggtgtccgat atcgcccggc tgtcctccta caccaactac     180
gccgactccg tgaagggccg gttcaccatc tcccgggaca actccaagaa caccctgtac     240
ctgcagatga actccctgcg ggccgaggac accgccgtgt actactgtgc cagaggcctg     300
gacgccagac ggatggacta ttggggccag ggcacccctgg tcaccgtcag ctca          354

<210> SEQ ID NO 4
<211> LENGTH: 339
<212> TYPE: DNA
<213> ORGANISM: Artificial Sequence
<220> FEATURE:
<223> OTHER INFORMATION: 005-C04-mat3-VL

<400> SEQUENCE: 4
cagtccgtgc tgacccagcc tccttccgcc tctggcaccc ctggccagag agtgaccatc      60
tcctgcaccg gctcctccag caacatcggc gctggctacg tggtgcactg gtatcagcag     120
ctgcccggca cgccccccaa gctgctgatc taccggaaca accagcggcc ctccggcgtg     180
cccgacagat tctccggctc caagtccggc acctccgcct ccctggccat ctccggcctg     240
agatctgagg acgaggccga ctactactgc gccgcctggg acgactccct gaacggctgg     300
ctgttcggcg gaggcaccaa gttaaccgtg ctgggccag                            339

<210> SEQ ID NO 5
<211> LENGTH: 8
<212> TYPE: PRT
<213> ORGANISM: Artificial Sequence
<220> FEATURE:
<223> OTHER INFORMATION: 005-C04-mat3-HCDR1

<400> SEQUENCE: 5

Phe Ser Ser Tyr Trp Met His Trp
1               5

<210> SEQ ID NO 6
<211> LENGTH: 19
<212> TYPE: PRT
<213> ORGANISM: Artificial Sequence
<220> FEATURE:
<223> OTHER INFORMATION: 005-C04-mat3-HCDR2

<400> SEQUENCE: 6

Ser Asp Ile Ala Arg Leu Ser Ser Tyr Thr Asn Tyr Ala Asp Ser Val
1               5                   10                  15

Lys Gly Arg
```

```
<210> SEQ ID NO 7
<211> LENGTH: 11
<212> TYPE: PRT
<213> ORGANISM: Artificial Sequence
<220> FEATURE:
<223> OTHER INFORMATION: 005-C04-mat3-HCDR3

<400> SEQUENCE: 7

Ala Arg Gly Leu Asp Ala Arg Arg Met Asp Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: 005-C04-mat3-LCDR1

<400> SEQUENCE: 8

Thr Gly Ser Ser Ser Asn Ile Gly Ala Gly Tyr Val Val His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: 005-C04-mat3-LCDR2

<400> SEQUENCE: 9

Arg Asn Asn Gln Arg Pro Ser
1               5

<210> SEQ ID NO 10
<211> LENGTH: 12
<212> TYPE: PRT
<213> ORGANISM: Artificial Sequence
<220> FEATURE:
<223> OTHER INFORMATION: 005-C04-mat3-LCDR3

<400> SEQUENCE: 10

Cys Ala Ala Trp Asp Asp Ser Leu Asn Gly Trp Leu
1               5                   10

<210> SEQ ID NO 11
<211> LENGTH: 453
<212> TYPE: PRT
<213> ORGANISM: Macaca fascicularis

<400> SEQUENCE: 11

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
                20                  25                  30

Pro Thr Asn Tyr Ser Leu Thr Tyr His Arg Glu Gly Glu Thr Leu Met
            35                  40                  45

His Glu Cys Pro Asp Tyr Ile Thr Gly Gly Pro Asn Ser Cys His Phe
        50                  55                  60

Gly Lys Gln Tyr Thr Ser Met Trp Arg Thr Tyr Val Met Met Val Asn
65                  70                  75                  80

Ala Thr Asn Gln Met Gly Ser Ser Phe Ser Asp Glu Leu Tyr Val Asp
                85                  90                  95
```

```
Val Thr Tyr Ile Val Gln Pro Asp Pro Pro Leu Glu Leu Thr Val Glu
            100                 105                 110

Val Lys Gln Pro Glu Asp Arg Lys Pro Tyr Leu Trp Met Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Thr His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Ile Met
        195                 200                 205

Asn Asp Ile Glu Gly Arg Met Asp Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys His
        435                 440                 445

His His His His His
    450

<210> SEQ ID NO 12
<211> LENGTH: 222
<212> TYPE: PRT
<213> ORGANISM: Homo sapiens

<400> SEQUENCE: 12

Gln Leu Pro Pro Gly Lys Pro Glu Ile Phe Lys Cys Arg Ser Pro Asn
1               5                   10                  15
```

```
Lys Glu Thr Phe Thr Cys Trp Trp Arg Pro Gly Thr Asp Gly Gly Leu
            20                  25                  30

Pro Thr Asn Tyr Ser Leu Thr Tyr His Arg Glu Gly Glu Thr Leu Met
        35                  40                  45

His Glu Cys Pro Asp Tyr Ile Thr Gly Pro Asn Ser Cys His Phe
50                      55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Leu Glu Leu Ala Val Glu
                100                 105                 110

Val Lys Gln Pro Glu Asp Arg Lys Pro Tyr Leu Trp Ile Lys Trp Ser
            115                 120                 125

Pro Pro Thr Leu Ile Asp Leu Lys Thr Gly Trp Phe Thr Leu Leu Tyr
130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn Asp Ile Glu Gly Arg Met Asp His His His His His
    210                 215                 220

<210> SEQ ID NO 13
<211> LENGTH: 222
<212> TYPE: PRT
<213> ORGANISM: Mus musculus

<400> SEQUENCE: 13

Gln Ser Pro Pro Gly Lys Pro Glu Ile His Lys Cys Arg Ser Pro Asp
1               5                   10                  15

Lys Glu Thr Phe Thr Cys Trp Trp Asn Pro Gly Ser Asp Gly Gly Leu
            20                  25                  30

Pro Thr Asn Tyr Ser Leu Thr Tyr Ser Lys Glu Gly Glu Lys Asn Thr
        35                  40                  45

Tyr Glu Cys Pro Asp Tyr Lys Thr Ser Gly Pro Asn Ser Cys Phe Phe
50                      55                  60

Ser Lys Gln Tyr Thr Ser Ile Trp Lys Ile Tyr Ile Thr Val Asn
65                  70                  75                  80

Ala Thr Asn Glu Met Gly Ser Ser Thr Ser Asp Pro Leu Tyr Val Asp
                85                  90                  95

Val Thr Tyr Ile Val Glu Pro Glu Pro Pro Arg Asn Leu Thr Leu Glu
                100                 105                 110

Val Lys Gln Leu Lys Asp Lys Lys Thr Tyr Leu Trp Val Lys Trp Leu
            115                 120                 125

Pro Pro Thr Ile Thr Asp Val Lys Thr Gly Trp Phe Thr Met Glu Tyr
130                 135                 140

Glu Ile Arg Leu Lys Ser Glu Glu Ala Asp Glu Trp Glu Ile His Phe
145                 150                 155                 160

Thr Gly His Gln Thr Gln Phe Lys Val Phe Asp Leu Tyr Pro Gly Gln
```

```
                    165                 170                 175
Lys Tyr Leu Val Gln Thr Arg Cys Lys Pro Asp His Gly Tyr Trp Ser
                180                 185                 190

Arg Trp Gly Gln Glu Lys Ser Ile Glu Ile Pro Asn Asp Phe Thr Leu
            195                 200                 205

Lys Asp Ile Glu Gly Arg Met Asp His His His His His
        210                 215                 220

<210> SEQ ID NO 14
<211> LENGTH: 124
<212> TYPE: PRT
<213> ORGANISM: Artificial Sequence
<220> FEATURE:
<223> OTHER INFORMATION: VH protein

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Asn Tyr Tyr Ala Thr Tyr Tyr Tyr Ala Met Asp
            100                 105                 110

Tyr Trp Gly Gln Gly Thr Leu Val Thr Val Ser Ser
        115                 120

<210> SEQ ID NO 15
<211> LENGTH: 113
<212> TYPE: PRT
<213> ORGANISM: Artificial Sequence
<220> FEATURE:
<223> OTHER INFORMATION: VL protein

<400> SEQUENCE: 15

Asp Ile Val Leu Thr Gln Ser Pro Asp Ser Leu Ala Val Ser Leu Gly
1               5                   10                  15

Glu Arg Ala Thr Ile Asn Cys Lys Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Pro Val Gln Ala Glu Asp Val Ala Thr Tyr Tyr Cys Gln His Ser Gly
                85                  90                  95

Glu Leu Pro Pro Ser Phe Gly Gln Gly Thr Lys Leu Glu Ile Lys Arg
            100                 105                 110

Ala
```

```
<210> SEQ ID NO 16
<211> LENGTH: 372
<212> TYPE: DNA
<213> ORGANISM: Artificial Sequence
<220> FEATURE:
<223> OTHER INFORMATION: VH DNA

<400> SEQUENCE: 16
gaggtgcagc tcgtggagtc tggcggcgga ctggtgcagc ctggcggcag cctgagactg      60
agctgcgccg tgagcggctt caccttcagc agctacggca tgagctgggt gcgccaggct     120
cctggcaagg gactggaatg ggtggccacc gtgtccagcg gcggcaccta cacctactac     180
cccgacagcg tgaagggccg gttcaccatc agccgggaca cagcaagaa caccctgtac      240 ctgcagatga acagcctgcg ggccgaggac accgccgtgt actactgcgc cagacaccgg     300
ggcaactact acgccaccta ctactatgcc atggactact ggggccaggg caccctggtg     360
accgtgagct ca                                                         372

<210> SEQ ID NO 17
<211> LENGTH: 339
<212> TYPE: DNA
<213> ORGANISM: Artificial Sequence
<220> FEATURE:
<223> OTHER INFORMATION: VL DNA

<400> SEQUENCE: 17
gatatcgtgc tgacccagag ccccgacagc ctggccgtga gcctgggcga gcgggccacc      60
atcaactgca aggccagcaa gtccgtgagc accagcggct acacctacat gcactggtat     120
cagcagaagc ccggccagcc ccccaagctg ctgatctacc tggccagcaa ccgggagagc     180
ggcgtgcccg accggtttag cggcagcggc tccggcaccg acttcaccct gaccatcagc     240
cccgtgcagg ccgaggacgt ggccacctac tactgccagc acagcggcga gctgccccccc    300 agcttcggcc agggcaccaa gctggaaatc aagcgggcc                            339
```